(12) United States Patent
Gao et al.

(10) Patent No.: US 11,414,477 B2
(45) Date of Patent: Aug. 16, 2022

(54) METHODS FOR PREPARING ANTIBODIES WITH A DEFINED GLYCOSYLATION PATTERN

(71) Applicant: MedImmune, LLC, Gaithersburg, MD (US)

(72) Inventors: Changshou Gao, Gaithersburg, MD (US); Pamela Thompson, Gaithersburg, MD (US); Dorin Toader, Gaithersburg, MD (US); Nazzareno Dimasi, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 1005 days.

(21) Appl. No.: 16/072,982

(22) PCT Filed: Jan. 26, 2017

(86) PCT No.: PCT/US2017/015005
§ 371 (c)(1),
(2) Date: Jul. 26, 2018

(87) PCT Pub. No.: WO2017/132298
PCT Pub. Date: Aug. 3, 2017

(65) Prior Publication Data
US 2021/0214419 A1    Jul. 15, 2021

Related U.S. Application Data

(60) Provisional application No. 62/287,472, filed on Jan. 27, 2016.

(51) Int. Cl.
*C07K 16/00* (2006.01)
*C12N 5/071* (2010.01)
*C12N 9/10* (2006.01)

(52) U.S. Cl.
CPC ............ *C07K 16/00* (2013.01); *C12N 5/0682* (2013.01); *C12N 9/10* (2013.01); *C07K 2317/14* (2013.01); *C07K 2317/41* (2013.01); *C12N 2510/02* (2013.01)

(58) Field of Classification Search
CPC ......... C07K 16/00; C12N 5/0682; C12N 9/10
See application file for complete search history.

(56) References Cited

U.S. PATENT DOCUMENTS

| | | |
|---|---|---|
| 7,867,734 B2 | 1/2011 | Nakano |
| 2012/0122206 A1 | 5/2012 | Umana et al. |
| 2012/0322100 A1 | 12/2012 | Gerngross |
| 2013/0059318 A1 | 3/2013 | Kaneko et al. |
| 2015/0125443 A1 | 5/2015 | Crispin et al. |
| 2015/0274837 A1 | 10/2015 | Umana et al. |

FOREIGN PATENT DOCUMENTS

| | | |
|---|---|---|
| WO | 1999054342 A1 | 10/1999 |
| WO | 2002079255 A1 | 10/2002 |
| WO | WO2004/063344 A2 | 7/2004 |
| WO | 2014065661 A1 | 5/2014 |
| WO | WO2015/057065 A1 | 4/2015 |
| WO | WO2015/057066 A1 | 4/2015 |

OTHER PUBLICATIONS

Van Geel et al., Bioconjugate Chmeistry, 26(11), 2233-2242, 2015.*
North et al., "Glycomics Profiling of Chinese Hamster Ovary Cell Glycosylation Mutants Reveals N-Glycans of a Novel Size and Complexity", Journal Biological of Chemistry, Dec. 1, 2009, vol. 285, pp. 5759-5775.
Yoo et al., "Differences in N-glycan structures found on recombinant IgA1 and IgA2 produced in murine myeloma and CHO cell lines" mAbs, 2010, vol. 2, No. 3, p. 320-334.
Patnaik et al., "Lectin-Resistant CHO Glycosylation Mutants", Methods in Enzymology, 2006, vol. 416, p. 159-182.
M. Singer and P. Berg "Genes and Genomes" Mill Valley, CA: University Science Books, 1991 in the Russian language.
English translation of extract from M. Singer and P. Berg "Genes and Genomes" Mill Valley, CA: University Science Books, 1991.
Office Action dated Apr. 28, 2020 as issued in corresponding Russian application No. 2018128784.
English translation of Office Action dated Apr. 28, 2020 as issued in corresponding Russian application No. 2018128784.
M. Pasek et al.: "The N-acetyl-binding pocket of N-acetylglucosaminyltransferases also accommodates a sugar analog with a chemical handle at C2", Glycobiology, vol. 22, No. 3, Mar. 1, 2012, pp. 379-388.
Natalia Mercer et al.: "Use of Novel Mutant Galactosyltransferase for the Bioconjugation of Terminal N-Acetylglucosamine (GlcNAc) Residues on Live Cell Surface", Bioconjugate Chemistry, vol. 24, No. 1, Jan. 16, 2013, pp. 144-152.
Nishikaze Takashi et al.: "Reversible hydrazide chemistry-based enrichment for O-GlcNAc-modified peptides and glycopeptides having non-reducing GlcNAc residues", The Analyst Dec. 7, 2013, vol. 138, No. 23, Dec. 7, 2013, pp. 7224-7232.
Zhang Peiqing et al.: "CHO Glycosylation Mutants as Potential Host Cells to Produce Therapeutic Proteins with Enhanced Efficacy", Advances in Biochemical Engineering, Biotechnol, Springer, Berlin, DE, vol. 131, Jan. 1, 2013, pp. 63-87.
Olczak Mariusz et al.: "UDP-Gal/UDP-GlcNAc chimeric transporter complements mutation defect in mammalian cells deficient in UDP-Gal transporter", Biochemical and Biophyscial Research Communcations, Elsevier, vol. 434, No. 3, Apr. 10, 2013, pp. 473-478.
Oelmann et al., "Point Mutations Identified in Lec8 Chinese Hamster Ovary Glycosylation Mutants That Inactivate Both the UDP-galactose and CMP-sialic Acid Transporters", Journal of Biological Chemistry, 2001, p. 26291-26300, vol. 276, Issue 28.

* cited by examiner

*Primary Examiner* — Maryam Monshipouri

(57) ABSTRACT

The present disclosure relates to a process for preparing antibodies with a defined glycosylation pattern, in particular antibodies with a glycan terminating in an N-acetylglucosamine. The antibodies of the disclosure are suitable for use in a process to conjugate a payload thereto. The disclosure also extends to molecules obtained and obtainable from the process disclosed herein, novel molecules and intermediates, compositions comprising said molecules and uses of the molecules and compositions, particularly in treatment, for example in the treatment of cancer.

13 Claims, 15 Drawing Sheets

Specification includes a Sequence Listing.

Figure 1A    A diagrammatic representation of glycans
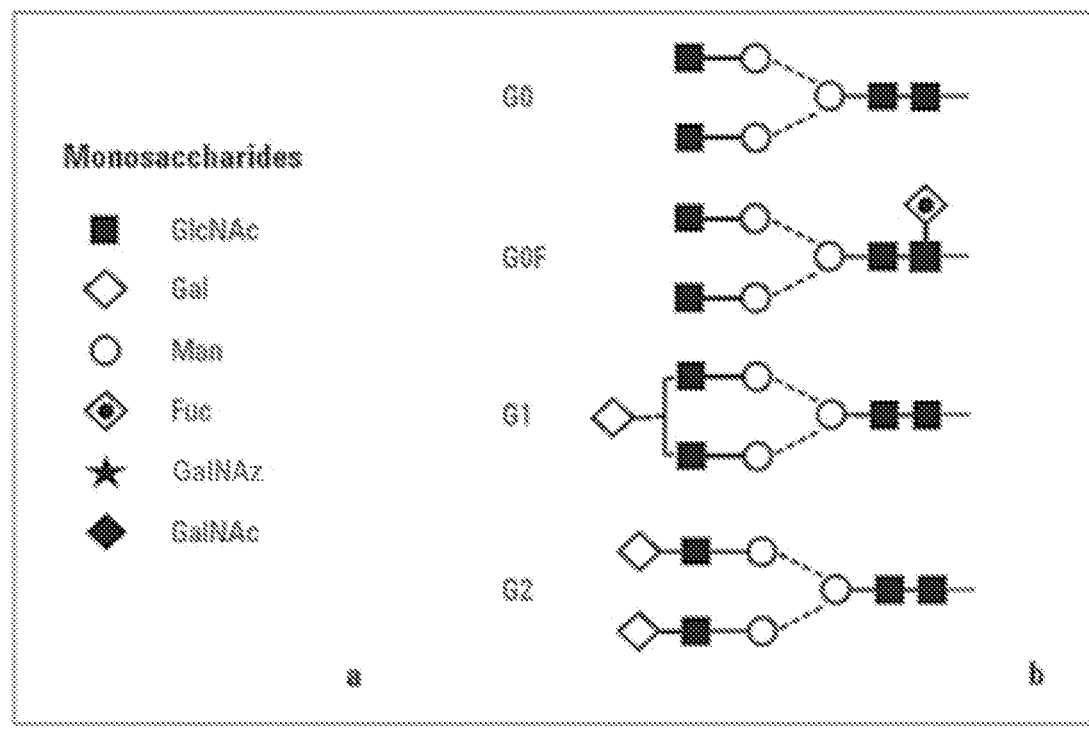
Figure 1B  Representation of Glycosylation on Antibodies
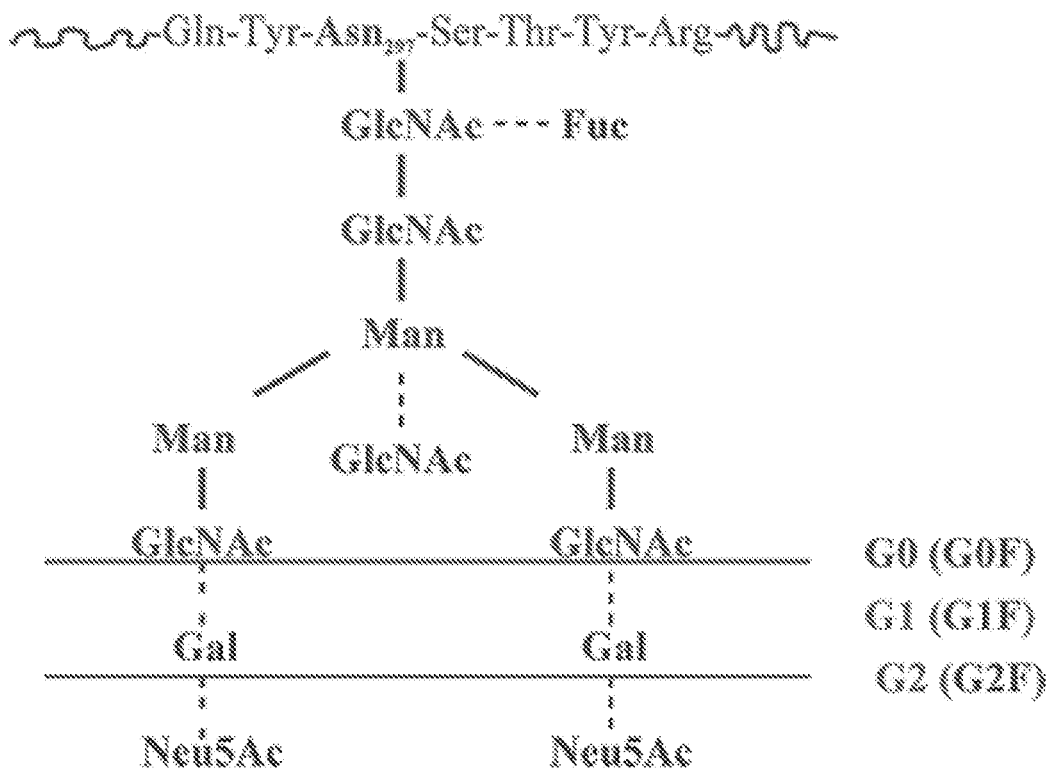

*N* and *O*-glycans and the effect on the same after synthesis in various Lec cells Figure 3   N-glycan structures for specific Lec Cell Expression Key: square is GlcNAc; circle is Man; Triangle is Fuc; and diamond is Gal Figure 4A    HPLC Analysis of CHO-LEC8 expressed IgG is in G0F form of Example Figure 4B shows the structure of the glycan on the IgG analysed in Figure 4A MALDI TOF Analysis of G0F antibody of Example 3

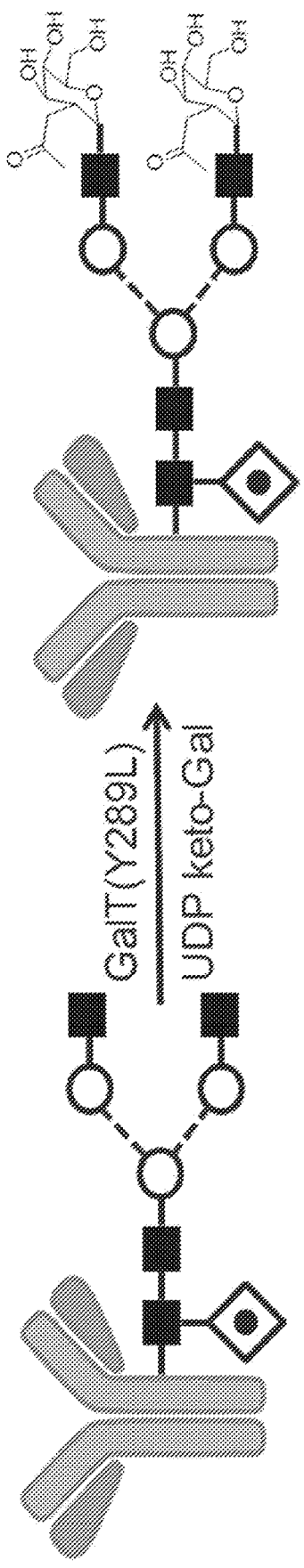
Figure 6A  Schematic to show transfer or reactive sugar to provide mAb-KETO-GAL from Example 4

Figure 6B    Mass Spec of Antibody before transfer of Keto-Gal
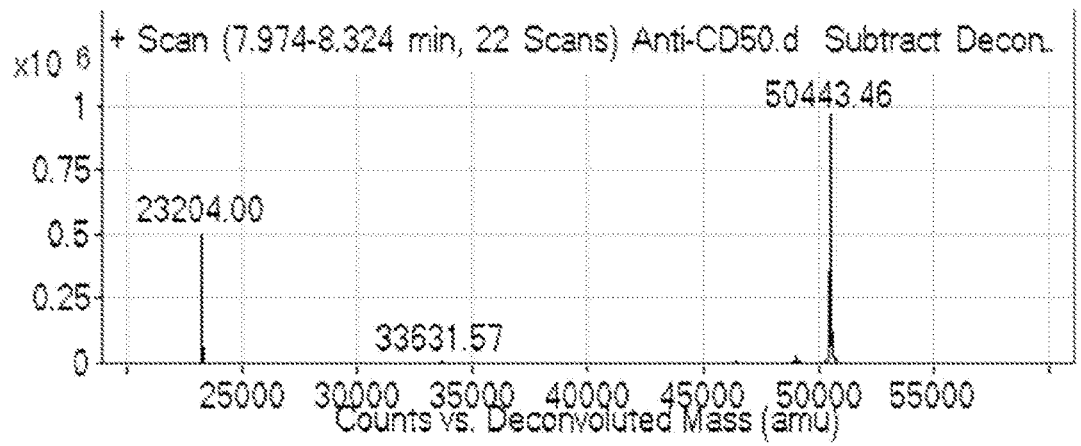
Figure 6c    Mass Spec of Antibody before transfer of Keto-Gal
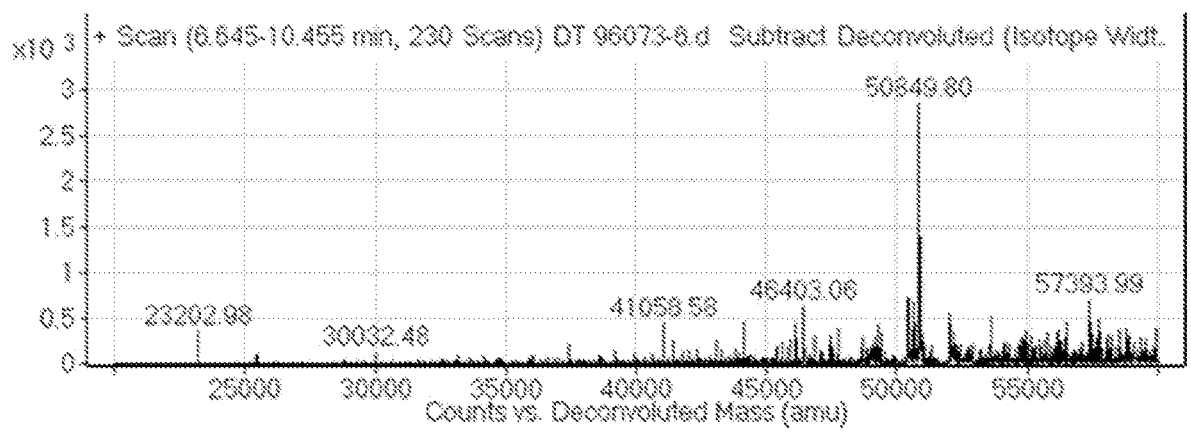

MALDI TOF Analysis after the Addition of GalNAz and Before Conjugation

MALDI TOF Analysis after Conjugation

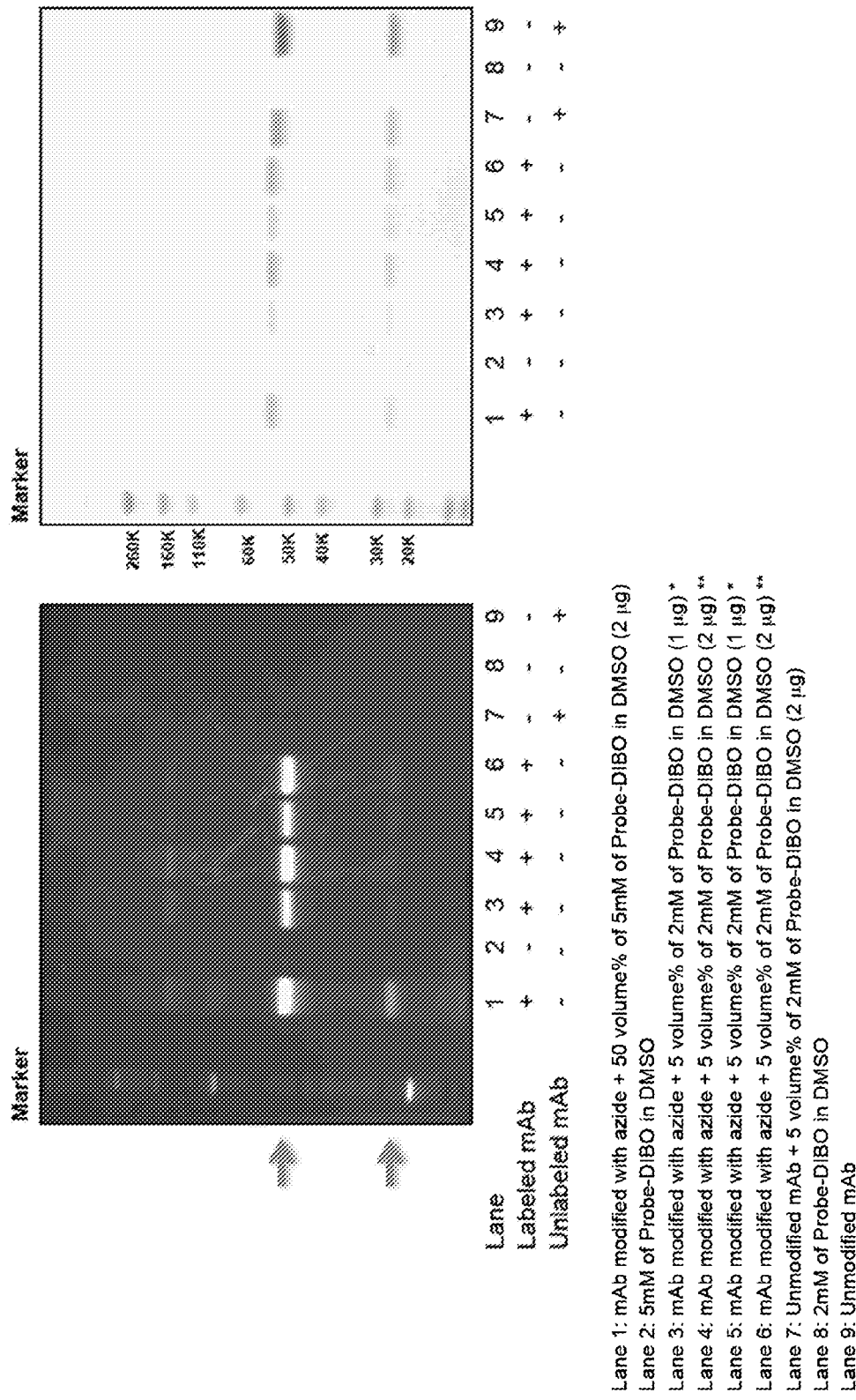

Figure 9

Lane 1: mAb modified with azide + 50 volume% of 5mM of Probe-DIBO in DMSO (2 μg)
Lane 2: 5mM of Probe-DIBO in DMSO
Lane 3: mAb modified with azide + 5 volume% of 2mM of Probe-DIBO in DMSO (1 μg) *
Lane 4: mAb modified with azide + 5 volume% of 2mM of Probe-DIBO in DMSO (2 μg) **
Lane 5: mAb modified with azide + 5 volume% of 2mM of Probe-DIBO in DMSO (1 μg) *
Lane 6: mAb modified with azide + 5 volume% of 2mM of Probe-DIBO in DMSO (2 μg) **
Lane 7: Unmodified mAb + 5 volume% of 2mM of Probe-DIBO in DMSO (2 μg)
Lane 8: 2mM of Probe-DIBO in DMSO
Lane 9: Unmodified mAb Mass Spectrums of an Antibody Expressed by Lec8 after transfer of a Reactive Sugar GalNAz by mutant GalT After Conjugation of the Antibody of Figure 10A to DBCO-Fluor® 488 through the reactive sugar by click chemistry Figure 11 Optimization of transfer Conditions
A      Concentration of mutant galactosyltransferase (GalT)
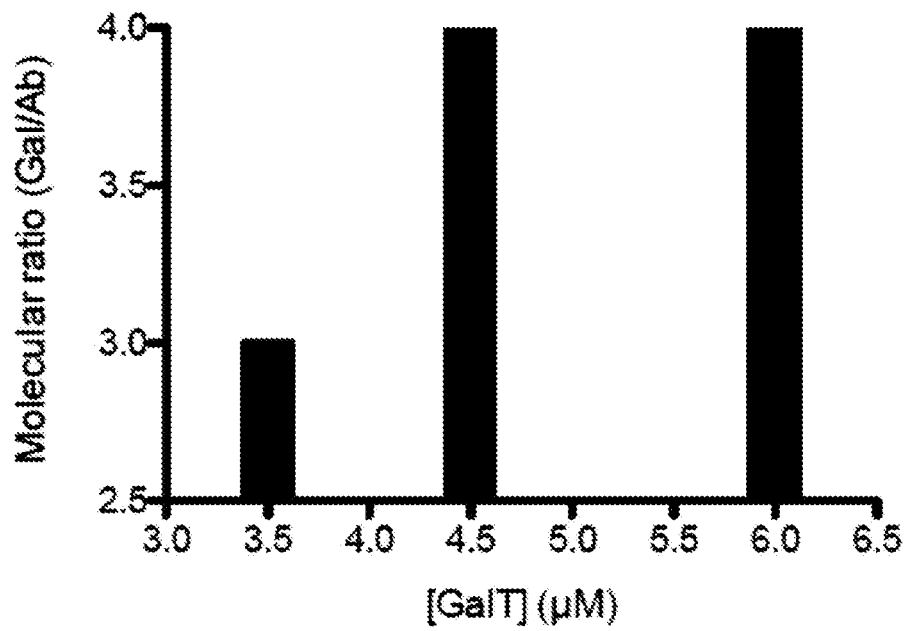
B      Concentration of UDP-GalNAz
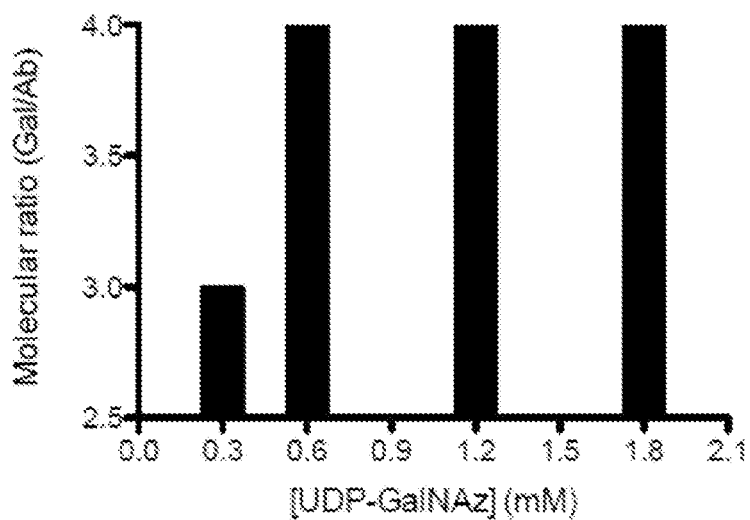

Figure 12 Influence of the number of equivalents of Fluorophore-DIBO on the molecular ratio of the product obtained from the conjugation of the antibody to the payload
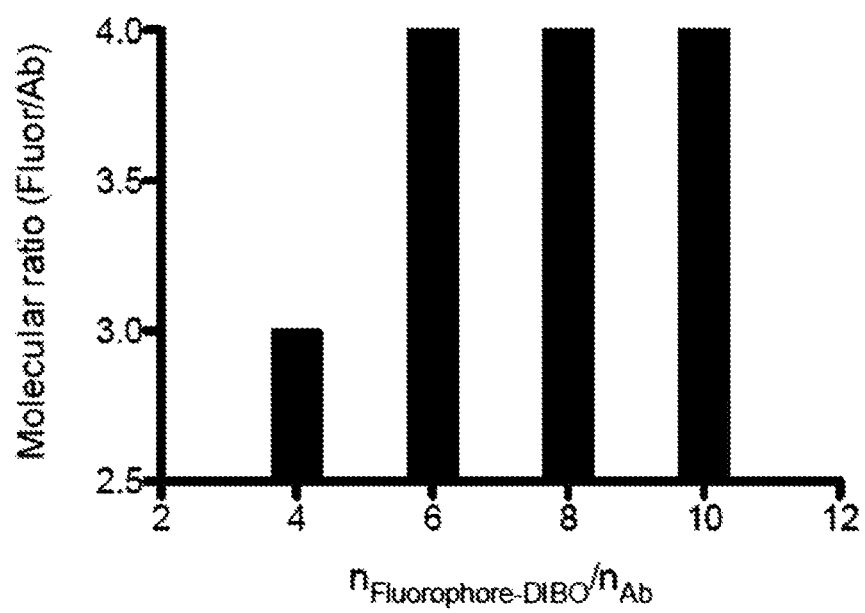

METHODS FOR PREPARING ANTIBODIES WITH A DEFINED GLYCOSYLATION PATTERN

The present disclosure relates to a process for preparing antibodies with a defined glycosylation pattern, in particular antibodies with a glycan terminating in an N-acetylglucosamine. The antibodies of the disclosure are suitable for use in a process to conjugate a payload thereto. The disclosure also extends to molecules obtained and obtainable from the process disclosed herein, novel molecules and intermediates, compositions comprising said molecules and uses of the molecules and compositions, particularly in treatment, for example in the treatment of cancer.

CROSS-REFERENCE TO RELATED APPLICATIONS

This application is a U.S. National Stage application of International Application No. PCT/US2017/015005, filed on Jan. 26, 2017, said International Application No. PCT/US2017/015005 claims benefit under 35 U.S.C. § 119(e) of the U.S. Provisional Application No. 62/287,472, filed Jan. 27, 2016. Each of the above listed applications is incorporated by reference herein in its entirety for all purposes.

REFERENCE TO THE SEQUENCE LISTING

This application incorporates by reference a Sequence Listing submitted with this application as text file entitled CONJ-101-WO-PCT_SL.TXT, created on Jul. 26, 2018, and having a size of 4.00 kilobytes.

BACKGROUND

Antibodies have become a very important category of therapeutics, which have provided significant advances in the treatment of patients. In 2012 five of the top twenty best selling drugs were antibodies. Conjugated antibodies are likely to form a significant part of second generation antibody products.

Antibody manufacture is relatively complicated and expensive. Usually a mammalian cells line, such as a CHO cell line, is employed to express the antibody to ensure proper folding and activity.

A post-translational modification of antibodies manufactured in CHO cells is glycosylation. Glycosylation is relevant to the immune recognition of antibodies and can influence the immunogenicity of a given antibody and other properties, such as effector function. What is more the antibody glycosylation for a given antibody may not be homogenous. This can lead to the molecular weight of the antibody falling within a range as opposed to being a discrete value.

Gradually the regulatory standards for biological products, such as antibodies are being raised. It may be necessary in the future to provide new antibody products where the glycosylation is controlled or defined.

Thus it would be useful to be able to manufacture antibodies with a defined glycosylation pattern. What is more if the structure of the glycosylation could be controlled then the antibody could be provided in a suitable format for further processing, for example conjugating the antibody to a payload.

WO2004/063344 discloses where glycans are converted into the G0 form (a particular glycan form) by treatment with the enzyme galactosidase. This enzymatic treatment removes any terminal galactose sugar residues and leaves a terminal N-acetylglucosamine sugar residue. Thus whilst in theory enzymes such as beta-1,4 galactosidase and other enzymes such as EndoS may be used to modify glycans on antibodies, there are several difficulties with this approach. Some problems are more acute at the commercial manufacturing scale than the laboratory or research scale. For processes performed on the commercial manufacturing scale it can be difficult to secure sufficient quantities of pure active enzyme. This is because for optimal activity the enzyme has to expressed in a natural conformation with proper folding. Furthermore the enzyme needs to be stored and transported under appropriate conditions to ensure the activity is retained. In addition subjecting antibodies to a cleaving enzyme, such as EndoS, has the potential to interfere with the folding and the activity of the antibody. Even if these aspects can be managed the step of subjecting the antibody to preparative enzyme treatment at a commercial scale leads to increased processing times, use of increased materials and increased man hours all of which have implications for the cost of goods.

Thus for an antibody manufacturing process on the commercial scale it is undesirable to employ an enzyme treatment step to cleave the glycans to provide a homogeneous antibody product.

Furthermore, it would be useful to have a site specific conjugation method that does not require modification of the basic amino acid sequence of the polypeptide or protein.

In addition it would be useful to avoid the use of metal and inorganic catalysts in the conjugation reaction as these catalysts can become contaminants that are difficult to remove in the final pharmaceutical product. The removal of these types of contaminants can require additional purification steps and sometimes even after additional purification it is difficult to get the contamination down to sufficiently low levels, to satisfy the requirements of the regulatory bodies.

The present inventors have identified a method which does not require an enzyme treatment step and can be employed without modifying the basic amino acid sequence of the antibody. Furthermore, conjugation of the antibody to a payload can be effected without recourse to copper catalysed chemistry.

SUMMARY OF THE DISCLOSURE

Thus in one aspect there is provided a method comprising expressing an antibody from a CHO glycosylation mutant cell line encoding said antibody, wherein said CHO cell line is mutated such that N-glycans on antibodies expressed by the cell have a terminal sugar which is N-acetyl glucosamine, for example where all the terminal sugar residues of N-glycans on antibodies expressed by the cell are N-acetyl glucosamine.

In one embodiment the cell line is a Lectin-Resistant CHO mutant cell line or CHO cell line with a mutation effective in a corresponding glycan synthetic pathway, for example Lec3.2.8, Lec4.8, Lec4A.8, Lec8, Lec10.8, Lec19 and Lec20, such as Lec3.2.8, Lec4.8, Lec4A.8, Lec8 and Lec10.8. These cells lines generally have mutations which affect their N-glycan synthesis pathways, for example a mutation which provides at least downregulation in UDP-Gal Golgi transporter.

In one embodiment the cell line is Lec8 or a CHO with a corresponding mutation or mutations in a relevant N-glycan synthesis pathway.

In one embodiment the mutation is in the gene Slc35a, such as Slc35a1, Slc35a2 or both, in particular a mutation in at least Slc35a2. Further mutations may include those in one or more genes selected from Mgat3, Mgat5, Gne and combinations thereof.

Alternative or additional mutations may comprise downregulation or inactivation of a B4galt gene, such as B4galt1, B4galt6 and combinations thereof. These mutations lead to downregulation of β4GalT-1 and β-1, 4-galactosyl transferases.

In one embodiment the mutation results in one or more of the following properties downregulation in CMP-sialic acid Golgi transporter, downregulation or mislocalization of GlcNAc-TV and/or upregulation of GlcNAc-TIII.

In one embodiment the mutated CHO cell line provides glycosylated antibodies wherein an N-glycan is attached through the amino acid Asn297 in the constant region of the antibody heavy chain.

Alternatively or additionally, an amino acid, such as asparagine (Asn) may be engineered into the antibody, for example in the hinge or constant region to provide a substrate for N-glycosylation.

In one embodiment the cell line is a manufacturing cell line, modified to comprise a mutation in an N-glycan synthetic pathway, in particular a mutation described herein. Manufacturing cell lines include, for example CHO S cell lines and the cell lines disclosed in WO2011/036455, WO2011/086136, WO2011/086138, WO2011/086139 and WO2013/007388.

The present disclosure in an independent aspect extends to a manufacturing cell modified in an N-glycan synthetic pathway, and processes for preparing the same.

In one embodiment the process comprises a further step of extending an N-acetyl glucosamine terminating glycan in an antibody according to the present disclosure by transferring onto the glycan a reactive sugar comprising a conjugation substrate (also referred to herein as a chemical functional group). This transfer may, for example be effected employing a transferase such as a Gal-transferase to transfer a reactive sugar specifically to a terminal N-acetyl glucosamine on the glycan.

In one embodiment the transferase is a GalT enzyme including mutated versions thereof wherein one or two amino acids are replaced, deleted or added, for example selected from the group comprising Y289L, Y289F, Y289N, Y, Y289M, 289I and R228K, such as Y289L, see for example Bojarova et al *Glycobiology* 2009, 19, 509 incorporated herein by reference.

Advantageously the method results in high levels of specific conversion transferring the reactive sugar onto the glycan even when mild conditions are employed. In one or more embodiments the method of the present disclosure is efficient, for example in respect of yields obtained and/or the number of processes steps involved.

In one embodiment the reactive sugar is derived from galactosamine.

Generally, the reactive sugar comprises a chemical functional group selected from a ketone, alkynyl and azide, to which a payload can be conjugated.

In one embodiment a sugar residue is selected from: GalNAz:

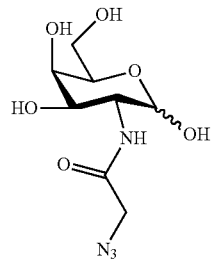

or a single enantiomer thereof, and
Keto-Gal:

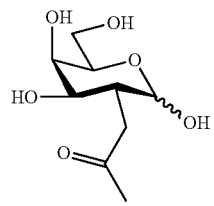

or a single enantiomer thereof.

The reactive galactose sugar residues above may represented herein as GalX where X is azide, keto, aldehyde or alkyne.

The sugar residue may be provided in the form of a UDP-sugar residue, for example GalNAz-UDP:

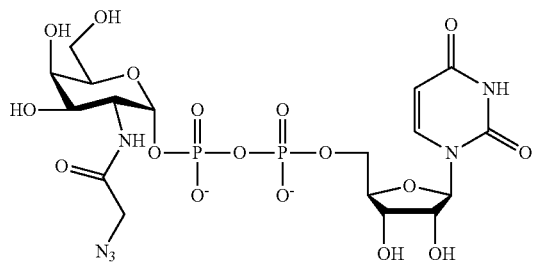

or a single enantiomer thereof, or
keto-Gal-UDP:

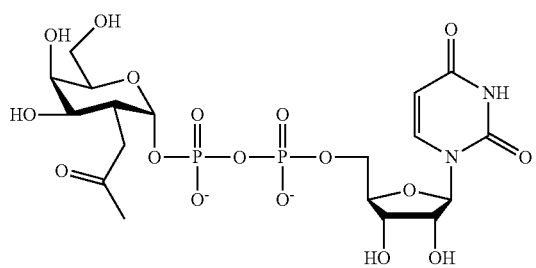

or a single enantiomer thereof.

In one embodiment the sugar residue is provided as UDP-Gal-alkyne.

The UDP acts as a leaving group in the transfer and the reactive sugar is specifically transferred to the N-acetyl glucosamine by the enzyme.

The subsequent conjugation is specific to the chemical function group in the reactive sugar now on the terminal of the glycan on the antibody and proceeds very efficiently without employing an inorganic catalyst. Advantageously this causes little disruption in the natural form and function of the antibody.

Thus in one embodiment the process of the present disclosure does not employ an inorganic catalyst, such as a copper catalyst in a conjugation reaction of the present disclosure.

Furthermore because the glycan on the antibody may be truncated by at least two saccharide/sugar molecules in comparison to naturally occurring glycans there is provided increased space for the payload. Thus the present method allows conjugation of large payloads without disrupting the antibody structure and/or function.

Thus in one embodiment the method comprises the further step of conjugating a payload to the chemical functional group in a reactive sugar residue on a glycan of an antibody molecule prepared according to the present disclosure.

In one embodiment the payload is selected from the group comprising a toxin, a drug molecule (such as cytotoxic agent), a polymer, an antibody or binding fragment thereof. In one embodiment the drug molecule is selected from the group comprising, for example a maytansinoid, for example N 2'-deacetyl-N 2'-(3-mercapto-1-oxopropyl)-maytansine (DM1), N 2'-deacetyl-N2'-(4-mercapto-1-oxopentyl)-maytansine (DM3) and N 2'-deacetyl-N 2'(4-methyl-4-mercapto-1-oxopentyl)-maytansine (DM4). In one embodiment the payload is a toxin. In one embodiment the payload is a polymer, for example the polymer is a natural polymer, such starch or albumin or a synthetic polymer, such as polyethylene (PEG).

In one embodiment the conjugating chemistry employed to join a payload to an antibody of the present disclosure is Click Chemistry, for example copper free Click Chemistry.

In one aspect the present disclosure extends to an antibody or antibody molecule obtained or obtainable from a method described herein and to compositions comprising same.

The present disclosure also extends to an antibody or antibody molecule or compositions disclosed herein, for use in treatment, particularly in the treatment of cancer.

DETAILED DESCRIPTION OF THE DISCLOSURE

CHO cell is a term of art understood by persons skilled in the art and as employed herein refers to cells derived from the ovaries of a Chinese hamster.

N-glycan as employed herein is a polysaccharide chain attached to the antibody, for example through the side chain of Asn, such as Asn297.

G0 glycan terminology as employed herein can be ascertained from the Figures. The term is employed generically to also refer to G0F structures, unless the context indicates otherwise. Generally the glycan structure starting from the amino acid to which the glycan is attached is: GlcNAc-GlcNAc-Man(Man-GlcNAc)Man-GlcNAc. The first GlcNAc may optionally bear a fucose residue and this is G0F. The first mannose residue may optionally bear a further GlcNAc residue.

The figures herein conflict in relation the exact structure of G1. However, the term as employed herein refers to where each branch of the structure G0 further comprise a galactose residue i.e. there are two galactose residues in the glycan. The G1F construct comprises a fucose residue on the first GlcNAc residue (analogous to G0F). The term G1 as employed herein generically refers to G1F unless the context indicates otherwise.

Defined glycosylation pattern as employed herein refers to, for example the ability to define and express the structure of a glycan or glycans in a recombinant protein, such as an antibody. In particular a defined glycosylation patterns ensures the majority of antibody molecules have the expected glycan structure (also referred to herein a glycosylation patterns).

In one embodiment 80, 85, 90, 91, 92, 93, 94, 95, 96, 97, 98, 99 or 100% of antibody molecules expressed have the expected or predicted glycan structure.

Thus in one aspect there is provided a population of antibodies with a defined glycosylation pattern, for example where the majority of antibodies in the population comprise a G0 glycan, such as where the antibody glycosylation pattern consists of a G0 glycan, in particular located on Asn297.

The parent cell line from which some Lec cell lines are derived is Pro⁻5, which has a genetic change resulting in no expression of B4galt6, see Lee et al J Biol Chem 2001, April 27; 276(17); 13924-34, incorporated herein by reference.

Lec 3.2.8 cell lines are down regulated in expression of CMP-sialic acid Golgi transporter and also UDP-Gal Golgi transporter. At the genetic level there is a mutation in the genes Gne and Slc35a1, and Slc35a2, see Hong and Stanley 2003 *J. Biol. Chem.* 278, 53045-53054, incorporated herein by reference.

Lec 4.8 cell lines are downregulated in expression of CMP-sialic acid Golgi transporter, UDP-Gal Golgi transporter, GlcNAc-TI, GlcNAc-TV and mislocalised GlcAc-TV. At the genetic level there is a deletion in Slc35a2 and Mgat5, see Olemann et al 2001 *J. Biol. Chem.* 276, 26291-26300, incorporated herein by reference.

Lec 4A.8 cell lines are down regulated in UDP-Gal Golgi transporter and mislocalized in relation to GlcAc-TV. At the genetic level there is a deletion in Slc35a2 and Mgat5, see Olemann et al 2001 *J. Biol. Chem.* 276, 26291-26300.

Lec 8 cell lines have downregulation in UDP-Gal Golgi transporter. At the genetic level they are mutated in Slc35a2 ORF, see Olemann et al 2001 *J. Biol. Chem.* 276, 26291-26300, incorporated herein by reference. Antibodies produced from this cell have an N-glycan terminating in N-acetyl glycosamine, i.e. are G0 or G0F glycans.

Lec 10.8 cell lines have downregulation in UDP-Gal Golgi transporter and upregulation in GlcNAc-TIII. At the genetic level there are mutations in Mgat3 and Slc35a2, see Stanley et al 1991 *Glycobiology* 1, 307-314, incorporated herein by reference.

Lec 19 is downregulated in β-1, 4-galactosyl-transferase. At the genetic level there is downregulation of expressions of six B4galt6 genes, see Lee et al 2003 Biochemistry 42, 12349-12357, incorporated herein by reference.

Lec 20 is downregulated in β4-GalT1. At the genetic level there is inactivation or downregulation of expression of the gene B4galt1 Lee et al 2001 *J. Biol. Chem.* 276, 13924-13934, incorporated herein by reference.

In one embodiment there is provided a mutated CHO cell line, for example a manufacturing cell line with at least one mutation independently selected from the group comprising a mutation wherein B4galtb is not expressed or not expressed in an active form; a mutation that provides the down regulation of CMP-sialic acid; a mutation that provides down regulation of UDP-Gal Golgi transporter; a mutation that provides down regulation of GlcNAc-TI; a mutation that provides down regulation of G1CNAC-TV and mislocalised GlcAc-TV; a mutation that provides down regulation of B-1,4 galactosyl-tranferase; a mutation that provides down regulation of β4-Galt1; and combination of two or more of said mutations.

In one embodiment there is provided a mutated CHO cell line, for example a manufacturing cell line wherein the mutation is in at least one gene independently selected from B4galt6; Gne; Slc35a1; Slc35a2; Mgat5; Mgat3; and combinations of two or more of the same.

Using only routine techniques there are many ways in which a skilled person can engineer a recombinant cell line, such as a CHO cell line to have the functionality described herein.

A manufacturing cell line as employed herein is a cell line that is well characterised and safe for the manufacture of recombinant proteins for use in human therapy, such as antibodies and binding fragments thereof. The cell line may have been approved by regulatory authorities, for example for use in the manufacture of antibodies. Generally manufacturing cell lines have been optimised for commercial scale manufacture and will usually provide "good" yields of recombinant proteins with the required folding and activity, such as antibodies and binding fragments thereof.

A mutated version of an enzyme as disclosed herein is an active enzyme where one or two (such as one) amino acid(s) in the enzyme sequence is/are independently replaced, added or deleted whilst retaining or enhancing the function of the enzyme in comparison to the wild-type unmutated enzyme. "Active enzyme" as employed herein is one which catalyses a reaction and has at least 50% of the activity of the corresponding unmutated enzyme (starting or wild-type enzyme).

Retaining or enhancing the function of the enzyme as employed herein refers to where the enzyme is an 'active enzyme as defined above' or where the mutated enzyme has greater activity or additional activity in comparison to the unmutated/wild-type enzyme. 'Additional activity' as employed herein is activity not possessed by the unmutated enzyme. Greater activity refers to an activity in the mutated enzyme which is increased; augment or improved in comparison to a corresponding unmutated enzyme.

In one embodiment the enzyme is a GalT enzyme i.e. galactose-1-phosphate uridylyltransferase (EC 2.7.7.12), for example GalT wild-type or a beta-(1,4)Gal-T1 mutant, such as where Y289 in the wild-type amino acid sequence is replaced by an alternative amino acid, in particular GalT (Y289L), GalT(Y289N), GalT(Y289F) and GalT(Y289M), more specifically GalT(Y289L). The mutated enzymes are able to transfer reactive sugars such as GalNAz (for example from UDP-GalNAz) and keto-Gal (for example from UDP-keto-Gal).

The terms "antibody" or "immunoglobulin," are used interchangeably herein and include whole full length antibodies and any antigen binding fragment, single chains thereof and multispecific (such as bispecific) antibody molecules comprising the same.

In one embodiment the GalT is recombinant. In one embodiment the enzyme is mammalian, for example human or bovine.

In one embodiment the antibody encoded and expressed according to the present disclosure comprises at least one, for example one N-glycosylation site, such as Asn297. In one embodiment an antibody of the disclosure comprises a CH2 domain or a fragment thereof comprising the Asn297 residue. In one embodiment the CH3 domain is present. In one embodiment the CH3 domain is absent.

In one embodiment an antibody molecule of the present disclosure comprise an Fc region.

The Fc region includes the polypeptides comprising the constant region of an antibody excluding the first constant region immunoglobulin domain, and fragments thereof. Thus, for IgG the "Fc region" refers to CH2 and CH3 and optionally all or a portion of the flexible hinge region N-terminal to these domains. The term "Fc region" can refer to this region in isolation, or this region in the context of an antibody, antibody fragment, or Fc fusion protein.

In one embodiment antibody molecule of the present disclosure comprises a light chain.

Each light chain is comprised of a light chain variable region (abbreviated herein as VL, VL region, or VL domain) and a light chain constant region. The light chain constant region is comprised of one domain, CL.

In one embodiment an antibody molecule of the disclosure comprises a heavy chain with a variable heavy region (abbreviated herein as VH, VH region or VH domain).

The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. Framework regions can be designated according to their respective VH and VL regions. Thus, e.g., VH-FW1 would refer to the first framework region of VH.

The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

A typical full length antibody comprises at least two heavy (H) chains and two light (L) chains interconnected by disulfide bonds. Each heavy chain comprises a heavy chain variable region (abbreviated herein as VH, VH region, or VH domain) and a heavy chain constant region. The heavy chain constant region comprises three or four constant domains, CH1, CH2, CH3, and CH4.

The term "antibody" means an immunoglobulin molecule or antigen binding fragment thereof that recognizes and specifically binds to a target, such as a protein, polypeptide, peptide, carbohydrate, polynucleotide, lipid, or combinations of the foregoing through at least one antigen recognition site (also referred to as a binding site) within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain antibody fragments (scFv and disulfide stabilized scFv (dsFv)), multispecific antibodies such as bispecific antibodies generated from at least two different antibodies or multispecific antibodies formed from antibody fragments (see, e.g, PCT Publications WO96/27011, WO2007/024715, WO2009018386, WO2009/080251, WO2013006544, WO2013/070565, and WO2013/096291), chimeric antibodies, humanized antibodies, human antibodies, fusion proteins comprising an antigen-binding fragment of an antibody, and any other modified immunoglobulin molecule comprising an antigen-binding fragment so long as the antibodies exhibit the desired biological activity.

An antibody can be of any of the five major classes of immunoglobulins: IgA, IgD, IgE, IgG, and IgM, or subclasses (isotypes) (e.g. IgG1, IgG2, IgG3, IgG4, IgA1 and IgA2), or allotype (e.g., Gm, e.g., G1m (f, z, a or x), G2m(n), G3m(g, b, or c), Am, Em, and Km(1, 2 or 3)). The different classes of immunoglobulins have different and well known subunit structures and three-dimensional configurations. Antibodies may be derived from any mammal, including, but not limited to, humans, monkeys, pigs, horses, llama, camels, rabbits, dogs, cats, mice, etc., or other animals such as birds (e.g. chickens).

The terms "antigen-binding fragment" refers to a fragment comprising antigenic determining variable regions of an intact antibody. It is known in the art that the antigen binding function of an antibody can be performed by fragments of a full-length antibody. Examples of antibody fragments include, but are not limited to Fab, Fab', F(ab')2, Fv fragments, scFvs, linear antibodies, single chain antibodies, and multispecific antibodies formed from antibody fragments.

Thus in one embodiment the antibody used in the present invention may comprise a complete antibody molecule having full length heavy and light chains or a fragment thereof and may be, but are not limited to Fab, modified Fab, Fab', modified Fab', F(ab')2, Fv, single domain antibodies (e.g. VH or VL or VHH), scFv, bi, tri or tetra-valent antibodies, Bis-scFv, diabodies, triabodies, tetrabodies, combinations of the same and epitope-binding fragments of any of the above.

However the antibodies and binding fragments thereof must comprise at least one glycosylation site, such as an N-glycosylation site.

In one embodiment the glycosylation site is not located in a CDR.

In one embodiment for small antibody binding fragments, such as scFvs the glycosylation site in engineered in the linker.

In one embodiment the antibody of the present disclosure is monoclonal.

Other antibodies specifically contemplated are "oligoclonal" antibodies which are a predetermined mixture of distinct monoclonal antibodies. See, e.g., PCT publication WO95/20401; U.S. Pat. Nos. 5,789,208 and 6,335,163. Suitably oligoclonal antibodies consist of a predetermined mixture of antibodies against one or more epitopes are generated in a single cell. More suitably oligoclonal antibodies comprise a plurality of heavy chains capable of pairing with a common light chain to generate antibodies with multiple specificities (e.g., WO04/009618). Oligoclonal antibodies are particularly useful when it is desired to target multiple epitopes on a single target molecule. Those skilled in the art will know or can determine what type of antibody or mixture of antibodies is applicable for an intended purpose and desired need.

Other binding proteins moieties specifically contemplated for use in the method of the present disclosure are small, engineered protein domains such as scaffold (see for example, US2003/0082630 and US2003/0157561). Scaffolds are based upon known naturally-occurring, non-antibody domain families, specifically protein extracellular domains, which typically of small size (~100 to ~300 AA) and containing a highly structured core associated with variable domains of high conformational tolerance allowing insertions, deletions or other substitutions. These variable domains can create a putative binding interface for any targeted protein. In general, the design of a generic protein scaffold consists of two major steps: (i) selection of a suitable core protein with desired features and (ii) generation of complex combinatorial libraries by mutagenizing a portion or all of the domains accepting high structural variability, display of these libraries in an appropriate format (i.e., phage, ribosome, bacterial, or yeast) and screening of the library for mutagenized scaffold having the desired binding characteristics (e.g. target specificity and/or affinity). The structure of the parental scaffolds can be highly diverse and include highly structured protein domains including but not limited to, FnIII domains (e.g., AdNectins, see, e.g., Protein Eng. Des. Sel. 18, 435-444 (2005), US2008/00139791, and WO 2005/056764, TN3, see e.g., WO2009/058379 and WO2011/130324); Z domains of protein A (Affibody, see, e.g., Protein Eng. Des. Sel. 17, 455-462 (2004) and EP1641818A1); domain A from LDL receptor (Avimers, see, e.g., Nature Biotechnology 23(12), 1556-1561 (2005) and Expert Opinion on Investigational Drugs 16(6), 909-917 (June 2007)); Ankyrin repeat domains (DARPins, J. Mol. Biol. 332, 489-503 (2003), PNAS (2003) and Biol. 369, (2007) and WO02/20565); C-type lectin domains (Tetranectins, see, e.g., WO02/48189). If desired two or more such engineered scaffold domains can be linked together, to form a multivalent binding protein. The individual domains can target a single type of protein or several, depending upon the use/disease indication.

The moieties discussed above require at least one glycosylation site, which if appropriate can be engineered into the recombinant molecule using routine methods.

Thus in one independent aspect here is provided a prestep of engineering into a binding protein molecule a suitable glycosylation site, for example an N-glycosylation site.

Virtually any molecule (or a portion thereof, e.g., subunits, domains, motifs or a epitope) may be targeted by an antibody including, but not limited to, integral membrane proteins including ion channels, ion pumps, G-protein coupled receptors, structural proteins; adhesion proteins such as integrins; transporters; proteins involved in signal transduction and lipid-anchored proteins including G proteins, enzymes such as kinases including membrane-anchored kinases, membrane-bound enzymes, proteases, lipases, phosphatases, fatty acid synthetases, digestive enzymes such as pepsin, trypsin, and chymotrypsin, lysozyme, polymerases; receptors such as hormone receptors, lymphokine receptors, monokine receptors, growth factor receptors, cytokine receptors; cytokines; and more.

In some aspects an antibody employed in the method of the present disclosure targets and/or incorporates all or a portion (e.g., subunits, domains, motifs or a epitope) of a growth factor, a cytokine, a cytokine-related protein, a growth factor, a receptor ligand or a receptor selected from among, for example, BMP1, BMP2, BMP3B (GDF10), BMP4, BMP6, BMP8, CSF1 (M-CSF), CSF2 (GM-CSF), CSF3 (G-CSF), EPO, FGF1 (αFGF), FGF2 (βFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, FGFR, FGFR1, FGFR2, FGFR3, FGFR4, FGFRL1, FGFR6, IGF1, IGF2, IGF1R, IGF2R, IFNA1, IFNA2, IFNA4, IFNA5, IFNA6, IFNA7, IFNAR1, IFNAR2, IFNB1, IFNG, IFNW1, FIL1, FIL1 (EPSILON), FIL1 (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, IL2RA, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL11RA, IL12RB1, IL12RB2, IL13RA1, IL13RA2, IL15RA, IL17R, IL17RA, IL17RB, IL17RC, IL17RD, IL18R1, IL20RA, IL20RB, IL21R, IL22R, IL22RA1, IL23R, IL27RA, IL28RA, PDGFA, PDGFB, PDGFRA, PDGFRB, TGFA, TGFB1, TGFB2, TGFB3, TGFBR1, TGFBR2, TGFBR3, ACVRL1, GFRA1, LTA (TNF-beta), LTB, TNF (TNF-alpha), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, TNFRSF1A, TNFRSF1B, TNFRSF10A (Trail-receptor), TNFRSF10B (Trail-receptor 2), TNFRSF10C (Trail-receptor 3), TNFRSF10D (Trail-receptor 4), FIGF (VEGFD), VEGF, VEGFB, VEGFC, KDR, FLT1, FLT4, NRP1, IL1HY1, IL1RAP, IL1RAPL1, IL1RAPL2, IL1RN, IL6 ST, IL18BP, IL18RAP, IL22RA2, AIF 1, HGF, LEP (leptin), PTN, ALK and THPO.

In some aspects an antibody employed in the method of the present disclosure targets and/or incorporates all or a portion (e.g., subunits, domains, motifs or a epitope) of a chemokine, a chemokine receptor, or a chemokine-related protein selected from among, for example, CCL1 (I-309), CCL2 (MCP-1/MCAF), CCL3 (MIP-1a), CCL4 (MIP-1b), CCL5 (RANTES), CCL7 (MCP-3), CCL8 (mcp-2), CCL11 (eotaxin), CCL13 (MCP-4), CCL15 (MIP-1d), CCL16 (HCC-4), CCL17 (TARC), CCL18 (PARC), CCL19 (MIP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCL1 (GRO1), CXCL2 (GRO2), CXCL3 (GRO3), CXCL5 (ENA-78), CXCL6 (GCP-2), CXCL9 (MIG), CXCL10 (IP 10), CXCL11 (I-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-1b), BLR1 (MDR15), CCBP2 (D6/JAB61), CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCP10, CKLFSF2, CKLFSF3, CKLFSF4, CKLFSF5, CKLFSF6, CKLFSF7, CKLFSF8, BDNF, C5R1, CSF3, GRCC10 (C10), EPO, FY (DARC), GDF5, HIF1A, IL8, PRL, RGS3, RGS13, SDF2, SLIT2, TLR2, TLR4, TREM1, TREM2, and VHL.

In some aspects an antibody employed in the method of the present disclosure targets and/or incorporates all or a portion (e.g., subunits, domains, motifs or a epitope) of a protein selected from among, for example renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; epidermal growth factor (EGF); insulin-like growth factor binding proteins; CD proteins such as CD2, CD3, CD4, CD 8, CD11a, CD14, CD18, CD19, CD20, CD22, CD23, CD25, CD33, CD34, CD40, CD40L, CD52, CD63, CD64, CD80 and CD147; erythropoietin; osteoinductive factors; immunotoxins; superoxide dismutase; T-cell receptors; surface membrane proteins; decay accelerating factor; viral antigen such as, for example, a portion of the AIDS envelope, e.g., gp120; transport proteins; homing receptors; addressins; regulatory proteins; cell adhesion molecules such as LFA-1, Mac 1, p150.95, VLA-4, ICAM-1, ICAM-3 and VCAM, a4/p7 integrin, and (Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD 18, CD61, CD104, beta5, beta6, beta7 and beta8; Integrin subunit combinations including but not limited to, $\alpha V\beta 3$, $\alpha V\beta 5$ and $\alpha 4\beta 7$; a member of an apoptosis pathway; IgE; blood group antigens; flk2/flt3 receptor; obesity (OB) receptor; mpl receptor; CTLA-4; protein C; an Eph receptor such as EphA2, EphA4, EphB2, etc.; a Human Leukocyte Antigen (HLA) such as HLA-DR; complement proteins such as complement receptor CR1, C1Rq and other complement factors such as C3, and C5; a glycoprotein receptor such as GpIb$\alpha$, GPIIb/IIIa and CD200.

Also contemplated are antibodies that specifically bind and/or comprises cancer antigens including, but not limited to, ALK receptor (pleiotrophin receptor), pleiotrophin, KS ¼ pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as: CEA, TAG-72, C017-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 5T4 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16, NY-BR-16, HER2 antigen (p185HER2), and HER3; polymorphic epithelial mucin (PEM); malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; Myl; VIM-D5; D156-22 found in colorectal cancer; TRA-1-85 (blood group H); SCP-1 found in testis and ovarian cancer; C14 found in colonic adenocarcinoma; F3 found in lung adenocarcinoma; AH6 found in gastric cancer; Y hapten; Ley found in embryonal carcinoma cells; TL5 (blood group A); EGF receptor found in A431 cells; E1 series (blood group B) found in pancreatic cancer; FC10.2 found in embryonal carcinoma cells; gastric adenocarcinoma antigen; CO-514 (blood group Lea) found in Adenocarcinoma; NS-10 found in adenocarcinomas; CO-43 (blood group Leb); G49 found in EGF receptor of A431 cells; MH2 (blood group ALeb/Ley) found in colonic adenocarcinoma; 19.9 found in colon cancer; gastric cancer mucins; T5A7 found in myeloid cells; R24 found in melanoma; 4.2, GD3, D1.1, OFA-1, GM2, OFA-2, GD2, and M1:22:25:8 found in embryonal carcinoma cells and SSEA-3 and SSEA-4 found in 4 to 8-cell stage embryos; Cutaneous Tcell Lymphoma antigen; MART-1 antigen; Sialy Tn (STn) antigen; Colon cancer antigen NY-CO-45; Lung cancer antigen NY-LU-12 variant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; TUMOR-ASSOCIATED ANTIGEN CO-029; Tumor-associated antigens MAGE-C1 (cancer/testis antigen CT7), MAGE-B1 (MAGE-XP antigen), MAGE-B2 (DAM6), MAGE-2, MAGE-4a, MAGE-4b and MAGE-X2; Cancer-Testis Antigen (NY-EOS-1) and fragments of any of the above-listed polypeptides.

In one embodiment the method according to the present disclosure comprises a prestep of treating a glycosylated antibody expressed from a process of the present disclosure with a galactosidase enzyme or a mutated version thereof to ensure the glycan on the antibody is homogeneous. However, usually this step will not be required because the advantageously the antibody expressed by the method of the present disclosure is homogeneous in relation to the glycan post-translational modification pattern of the population of antibodies produced.

Substrate as employed herein refers to the molecule or fragment thereof upon which an enzyme acts, unless the context indicates otherwise.

In the present method the characterising entity in the substrate (onto which the reactive sugar is transferred by a transferase) is that it comprises a terminal N-acetyl glucosamine residue on an N-glycan connected to the antibody.

N-acetyl glucosamine has the following the structure:

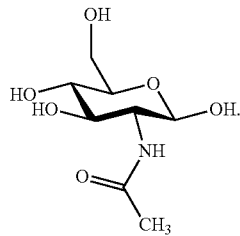

Reactive sugar as employed herein refers to a sugar residue comprising a chemical functions group, for example an azide, keto or alkynyl group that is capable of participating a chemical conjugation reaction, and through which ultimately the payload will be linked to the glycan on the antibody.

Chemical functional group in a sugar residue as employed herein is a group capable of conjugating via a chemical bond (in particular a co-valent bond) to a functional group in a payload.

Azide, keto, aldehyde and alkynyl are given their ordinary chemical meaning in the context of the present specification.

Usually the chemical functional group is appended to the sugar ring, such that the sugar retains its identity/designation (the latter is a based on the ring structure). Thus derived from a sugar, such as galactose as employed herein refers to where the original sugar ring structure is retained and the functional group is appended to the ring, see for example the synthetic routes provided in the Examples. Thus generally the functional group is not part of the architecture of the sugar ring.

Examples of chemistry capable of forming a suitable co-valent bond in a conjugation reaction are well known to those skilled in the art and include but are not limited to those exemplified below.

When the functional chemical group is an azide click chemistry, for example copper free click chemistry may be employed in combination with appropriate functionality in the payload for the conjugation, for example a DIBO modified payload may be employed.

Conjugated as employed herein refers to the joining of two compounds or molecules or fragments together by forming a chemical co-valent bond. Click Chemistry has been designed to rapidly conjugate two entities each comprising an appropriate chemical functional group.

It will be clear to persons skilled in the art that a pair of functional groups one in the antibody and one in the payload react to form a covalent bond and conjugate the two entities together, for example an azide may react with an alkyne in the conjugation reaction. When designing the antibodies and synthetic or semi-synthetic payload molecules there is a choice about which functional chemical group is incorporated into which entity.

In one embodiment an azide entity in a reactivity sugar is attached to a glycan on an antibody molecule of the present disclosure. In the corresponding payload the functional group may be one of multiple reaction partners suitable for reacting with azide including for example but not limited to alkynyl.

In one embodiment a keto functional group for example comprising —C(O)CH$_3$ in a reactive sugar attached to a glycan on an antibody of the present disclosure may be employed, for example in an oximation reaction to conjugate the antibody to the payload.

In one embodiment an aldehyde functional group in a reactive sugar attached to a glycan on an antibody of the present disclosure may be employed in a reaction with an amine in a payload such as a primary amine or secondary amine in the payload.

In one embodiment an alkynyl functional group in a reactive sugar attached to a glycan in an antibody of the present disclosure may be employed in a reaction with an azide in a payload, for example employing chemistry such as click chemistry, especially suitable is copper free click chemistry.

Click Chemistry

Examples of click chemistry conjugation reactions include those employing a molecule comprising an azide which reacts with, for example an component comprising a Click-mates™ alkyne, such as 5-propargyloxy-dU CEP, 5-octadiynyl-du CEP, alkynyl-modifier-C6-dT CEP, 5-(propargyloxy)-2'-deoxyuridine, 5-(1,7-octadiyn-1-yl)-2'-deoxyuridine, 5-octadiynyl-TMS-dU CEP, 5-octadiynyl-TMS-dC CEP, 5-octadiynyl-dC CEP, 5-octadiynyl-TIPS-dU CEP. This chemistry employs a copper catalyst and for pharmaceutical preparations it may be desirable to avoid there use of a copper catalyst.

As discussed above the antibody component can be designed to as required to contain the azide, aldehyde or alkyne functional group (in particular the azide or aldehyde functional group) and the payload can be designed to comprise the relevant conjugation partner. However, in one embodiment the payload comprises the alkyne functional group and the antibody comprises the azide functional group.

Reagents suitable for use in copper free reactions are available, for example from the Click-easy® alkynes which include BCN CEP I, BCN CEP II, BCN-N-hydroxysuccinimide ester I, BCN-N-hydroxysuccinimide ester II, MFCO-N-hydroxysuccinimide ester and MFCO CEP. These reagents generally react with an azide in a molecule of interest.

In one embodiment the alkyne click reagent, for example attached to a payload, is selected from OCT, DIFO, DIBO, BCN, BARAC, DIFBO, thiaOct, thiaDIFBO, TMTH, Dibenzocyclooctyl (DBCO) and

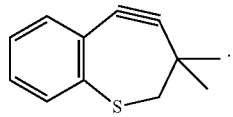

These reagents may for example be employed in a reaction of the type shown in the scheme below, where the biomolecule represents the antibody-glycan-reactive sugar and tag represents a payload:

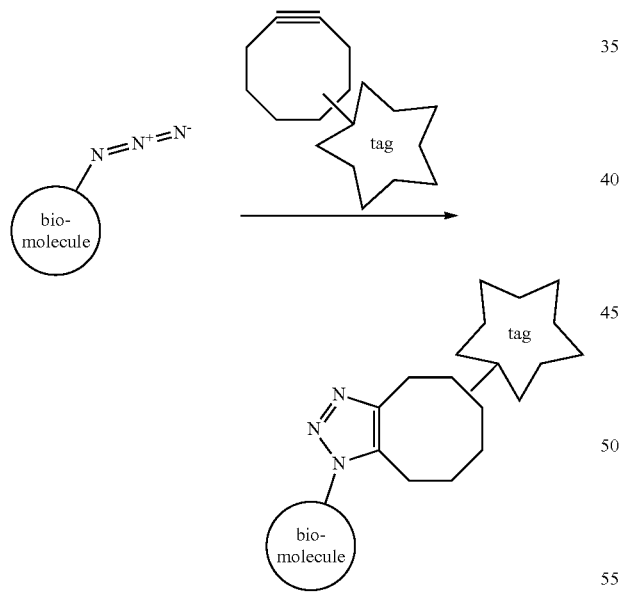

The chemical structure of these reagents is shown below:

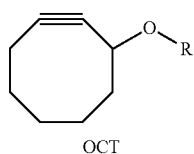

OCT

1

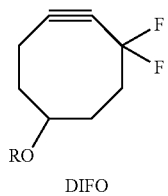

DIFO

2

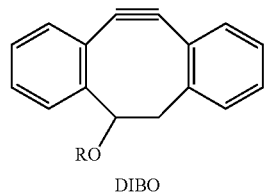

DIBO

3

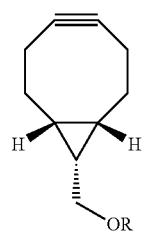

BCN

4

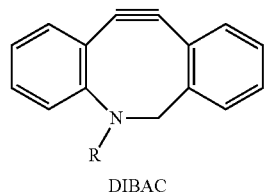

DIBAC

5

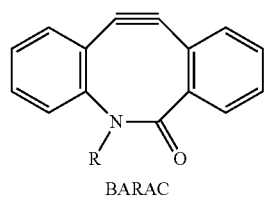

BARAC

6

DIFBO

7

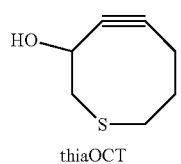

thiaOCT

8

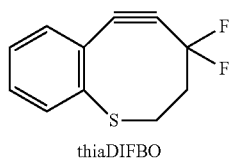

thiaDIFBO

9

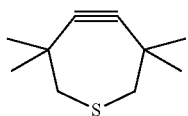

TMTH

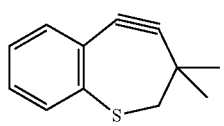

The structures shown are an extract from Thiacycloalkyne for Copper-Free Click Chemistry Angew. Chem Int Ed. 2012, 51, 2443-2447.)

DBCO has the following structure:

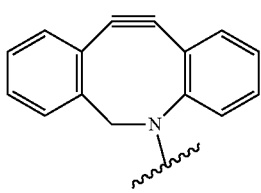 [SMILES: *N1Cc2ccccc2C#Cc2ccccc21]

In one embodiment fragments, for example comprising an alkyne as part of multiple ring system may be most suitable for incorporation in the payload.

In one embodiment the functional group in the payload is a derivative of a click chemistry reagent, for example biotin DIBO alkyne which has the following structure:

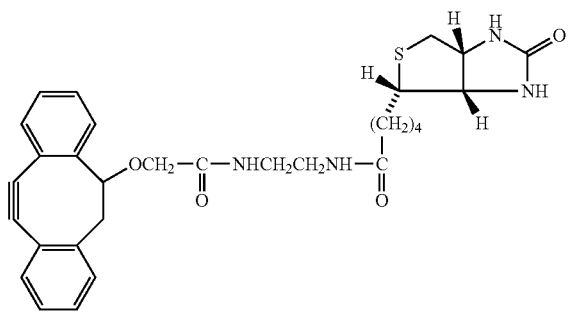

wherein the biotin is the payload.

Clearly the biotin can be replaced by any one of a large number of synthetic molecules, semisynthetic molecules, biological molecules, polymers, toxins, radionucleotides, fluorescent labels and the like.

Click-IT® maleimide DIBO alkyne is commercially available and the maleimide can be used to conjugate to DIBO to a desired payload.

In one embodiment the method the present disclosure employs copper free click chemistry in a conjugation step in a process according to the present disclosure, for example a conjugation step between the antibody of the present disclosure and a payload. A variety of copper free click chemistry reagents are commercially available and may be employed in a method according to the present disclosure. The following are available from Invitrogen (catalogue No. in parenthesis):

(C10405) Click-iT® DIBO-Alexa Fluor® 488 *for Cu-Free click chemistry*,
(C10406) Click-iT® DIBO-Alexa Fluor® 555 *for Cu-Free click chemistry*,
(C10407) Click-iT® DIBO-Alexa Fluor® 594 *for Cu-Free click chemistry*,
(C10408) Click-iT® DIBO-Alexa Fluor® 647 *for Cu-Free click chemistry*,
(C10410) Click-iT® DIBO TAMRA *for Cu-Free click chemistry*,
(C10411) Click-iT® DIBO amine *for Cu-Free click chemistry*,
(C10412) Click-iT® DIBO biotin *for Cu-Free click chemistry*,
(C10413) Click-iT® DIBO maleimide *for Cu-Free click chemistry*, and
(C10414) Click-iT® DIBO succinimidyl ester *for Cu-Free click chemistry*.

Related Products which comprise the relevant chemical function groups include the following fluorescent labels (i.e the latter is the payload): (A10044) EdU (5-ethynyl-2'-deoxyuridine): (A10266) Alexa Fluor® 488 azide (Alexa Fluor® 488 5-carboxamido-(6-azidohexanyl)bis(triethylammonium salt)): (A10267) Alexa Fluor® 488 alkyne (Alexa Fluor® 488 5-carboxamido-(propargyl), bis(triethylammonium salt)): (A20012) Alexa Fluor® 555 azide, triethylammonium salt, (A20013) Alexa Fluor® 555 alkyne, triethylammonium salt; (A10270) Alexa Fluor® 594 azide (Alexa Fluor® 594 carboxamido-(6-azidohexanyl), bis(triethylammonium salt)); (A10275) Alexa Fluor® 594 alkyne (Alexa Fluor® 594 carboxamido-(5-(and 6-)propargyl), bis(triethylammonium salt)); (A10277) Alexa Fluor® 647 azide, triethylammonium salt; (A10278) Alexa Fluor® 647 alkyne, triethylammonium salt; (A10279) alkyne, succinimidyl ester (3-propargyloxypropanoic acid, succinimidyl ester); (A10280) azido (PEO)4 propionic acid, succinimidyl ester (3-(azidotetra(ethyleneoxy))propionic acid, succinimidyl ester); (B10184) biotin azide; (B10185) biotin alkyne; (C10102) Click-iT® AHA (L-azidohomoalanine) *for nascent protein synthesis*; (C10186) Click-iT® HPG (L-homopropargylglycine) *for nascent protein synthesis*; (C10248) Click-iT® farnesyl alcohol, azide *mixed isomers*; (C10249) Click-iT® geranylgeranyl alcohol, azide *mixed isomers*; (C10264) Click-iT® fucose alkyne (tetraacetyl fucose alkyne); (C10265) Click-iT® palmitic acid, azide (15-azidopentadecanoic acid); (C10268) Click-iT® myristic acid, azide (12-azidododecanoic acid); (10269) Click-iT® Cell Reaction Buffer Kit; (C10276) Click-iT® Protein Reaction Buffer Kit; (C33365) Click-iT® GalNAz metabolic glycoprotein labeling reagent (tetraacetylated N-azidoacetylgalactosamine)-for O-linked glycoproteins; (C33366) Click-iT® ManNAz metabolic glycoprotein labeling reagent (tetraacetylated N-azidoacetyl-D-mannosamine)-*for sialic acid glycoproteins; (C33367) Click-iT® GlcNAz metabolic glycoprotein labeling reagent (tetraacetylated N-azidoacetylglucosamine)-for O-GlcNAC-modified proteins; (C33368) Click-iT® O-GlcNAc Enzymatic Labeling System-for O-linked GlcNAc glycoproteins; (C33370) Click-iT® Tetramethylrhodamine (TAMRA) Protein Analysis Detection Kit; (C33371) Click-iT® Dapoxyl® Protein Analysis Detection Kit; (C33372) Click-iT® Biotin Protein Analysis Detection Kit; (10187) EdU (5-ethynyl-2'-deoxyuridine); (110188) iodoacetamide azide; (110189) iodoacetamide alkyne; (010180) Oregon Green® 488 azide (Oregon Green® 488 6-carboxamido-(6-azidohexanyl), triethylammonium salt); (010181) Oregon Green® 488 alkyne *6-isomer; (T10182) tetramethylrhodamine (TAMRA)

azide (tetramethylrhodamine 5-carboxamido-(6-azidohexanyl)) *5-isomer*; (T10183) tetramethylrhodamine (TAMRA) alkyne (5-carboxytetramethylrhodamine, propargylamide)*5-isomer*.

In the event an alkynyl functional group is present in the reactive sugar attached to a glycan on an antibody of the present disclosure then, for example Click Mate's® azide chemistry may be employed in the payload. Suitable reagents for incorporating into the payload include: (BT-107s) Desthiobiotin-TEG azide; (BT-1085) Biotin-TEG azide; (FC-8150) Folate-TEG azide; (BT-8160) Tocopherol-TEG; (FD-13005) water soluble dansyl-TEG azide; (FF6110) 6-carboxyfluorescein-TEG azide; (LK4270) Aminooxy-TEG azide; (BL3030) BBQ-650™-TEG azide; (FF6130) 6-TET-TEG azide; (LK4310) amino-TEG azide; (FC8170) PQQ-TEG azide; (FC8180) Cholesteryl-TEG azide; (PS5030) Psoralen-TEG azide; (DB 8010) Dabcyl-TEG azide; (FC8190) DTPA-quinalone-TEG azide; (FC8200) azidocoumarin N-hydroxysuccinimide ester; (F8205) azidocourmarin-spacer-12-amine formate; (FC8210) azidocoumarin-space-6 formate; (FC 8215) azidocoumarin-spacer-12 maleimide.

Process Parameters

Process parameters after expression of the antibody may be employed to control the glycan and conjugated products obtained. As shown in FIG. 10 concentrations of mutated enzyme such as GalT can either be employed to add the reactive to sugar to all 4 possible N-glycan substrates available in the antibody. Thus concentrations of 4.0 μM and higher such as 4.5 μM of enzyme provide a molecular ratio of 4 reactive sugars per antibody.

A molecular ratio of 3 reactive sugars per antibody can be provided by employing an enzyme concentration of less than 4 μM, such a 3.5 μM.

The concentration of the reactive sugar reagent, for example UDP-GalNAz can also be employed to control the ratio of reactive sugar transferred to each antibody, for example, a concentration of 0.5 mM or higher provides a ratio of 4 reactive sugars per antibody. In contrast a concentration of about 0.4 mM and lower such as 0.3 mM provides a ratio of 3 reactive sugars per antibody molecule.

In one embodiment the molecular equivalents of payload employed in the conjugation reaction can be used to control ratio of payload obtained in the final product per antibody molecule, for example a ratio of 5 or greater, such as at least 6 payload molecules per antibody provides a final product with 4 payload molecules conjugated to the antibody. Of course this requires 4 reactive sugars to be present in each antibody molecule (and as discussed above this may or may not be the case). In contrast employing a ratio of less than 5 payload molecules per antibody in the conjugation reaction may be used to provide a final antibody conjugate with 3 payload molecules per antibody.

Payload Molecules

Payload as employed herein refers to a molecule or component (including a fragment or chemical entity), which is intended for "delivery" to a target region by conjugation to an antibody which 'guides' the same to the desired location. Generally the payload will be an effector molecule, for example selected from the group consisting of a toxin, such as a cytotoxin, including a chemotherapeutic agent, a drug, a pro-drug, an enzyme, an immunomodulator, an antiangiogenic agent, a pro-apoptotic agent, a cytokine, a hormone, an antibody or fragment thereof, synthetic or naturally occurring polymers, a polynucleotide or oligonucleotide and fragments thereof e.g. DNA, RNA and fragments thereof (e.g., an antisense molecule or a gene), radionuclides, particularly radioiodide, radioisotopes, chelated metals, nanoparticles and reporter groups such as fluorescent compounds or compounds which may be detected by NMR or ESR spectroscopy.

In one embodiment the payload is selected from the group comprising a toxin, drug, radionuclide, immunomodulator, cytokine, lymphokine, chemokine, growth factor, tumor necrosis factor, hormone, hormone antagonist, enzyme, oligonucleotide, DNA, RNA, siRNA, RNAi, microRNA, peptide nucleic acid, photoactive therapeutic agent, anti-angiogenic agent, pro-apoptotic agent, non-natural amino acid, peptide, lipid, a polymer, carbohydrate, scaffolding molecule, fluorescent tag, visualization peptide, biotin, serum half-life extender, capture tag, chelating agent, solid support, or a combination thereof.

In one embodiment the payload is a drug molecule (also referred to herein as a drug). Examples of drug molecules for use in the present disclosure include nitrogen mustard, ethylenimine derivative, alkyl sulfonates, nitrosourea, gemcitabine, triazene, folic acid analog, anthracycline, taxane, COX-2 inhibitor, pyrimidine analog, purine analog, antibiotic, enzyme inhibitor, epipodophyllotoxin, platinum coordination complex, vinca alkaloid, substituted urea, methyl hydrazine derivative, adrenocortical suppressant, hormone antagonist, endostatin, taxol, camptothecin, doxorubicin, doxorubicin analog, antimetabolite, alkylating agent, antimitotic, anti-angiogenic agent, tyrosine kinase inhibitor, mTOR inhibitor, heat shock protein (HSP90) inhibitor, proteosome inhibitor, HDAC inhibitor, pro-apoptotic agent, methotrexate, CPT-11, or a combination thereof, and wherein conjugation is.

In particular aspects, the drug is amifostine, cisplatin, dacarbazine, dactinomycin, mechlorethamine, streptozocin, cyclophosphamide, carrnustine, lomustine, doxorubicin lipo, gemcitabine, daunorubicin, daunorubicin lipo, procarbazine, mitomycin, cytarabine, etoposide, methotrexate, 5-fluorouracil, vinblastine, vincristine, bleomycin, paclitaxel, docetaxel, aldesleukin, asparaginase, busulfan, carboplatin, cladribine, 10-hydroxy-7-ethyl-camptothecin (SN38), gefitinib, dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil aromatase inhibitors, and combinations thereof.

In one embodiment the drug is selected from the group comprising alkylphosphocholines, topoisomerase I inhibitors, taxoids and suramin.

In one embodiment toxin refers to cytotoxins or cytotoxic agents including any agent that is detrimental to (e.g. kills) cells. Examples include aplidin, anastrozole, azacytidine, bortezomib, bryostatin-1, busulfan, combrestatins, carmustine, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In one embodiment the drug (also a cytotoxin in this instance) comprises an antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), carboplatin, anthracyclines (e.g. daunorubicin (formerly daunomycin) and doxorubicin or doxorubicin glucuronide), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

In some aspects, the drug is an auristatin (U.S. Pat. Nos. 5,635,483; 5,780,588), for example, MMAE (monomethyl auristatin E) or MMAF (monomethyl auristatin F). In other aspects, the drug is a dolastatin or dolastatin peptidic analog or derivative. Dolastatins and auristatins have been shown to interfere with microtubule dynamics, GTP hydrolysis, and nuclear and cellular division (Woyke et al., Antimicrob. Agents and Chemother. 45:3580-3584 (2001)) and have anticancer activity (U.S. Pat. No. 5,663,149). The dolastatin or auristatin drug moiety can be attached to the conjugate compound through the N (amino) terminus or the C (carboxyl) terminus of the peptidic drug moiety. See WO2002/088172, which is herein incorporated by reference in its entirety.

In other aspects, the drug is a maytansinoid. In some aspects, the maytansinoid is N 2'-deacetyl-N 2'-(3-mercapto-1-oxopropyl)-maytansine (DM1), N 2'-deacetyl-N2'-(4-mercapto-1-oxopentyl)-maytansine (DM3) or N 2'-deacetyl-N 2'(4-methyl-4-mercapto-1-oxopentyl)-maytansine (DM4). Maytansinoids are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, which are herein incorporated by reference in their entireties.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines. Conjugates containing maytansinoids, methods of making same, and their therapeutic use are disclosed, for example, in U.S. Pat. Nos. 5,208,020, 5,416,064 and EP0425235; Liu et al., Proc. Natl. Acad. Sci. USA 93:8618-8623 (1996) (described immunoconjugates comprising a maytansinoid designated DM1); and Chari et al., Cancer Research 52:127-131 (1992), which are herein incorporated by reference in their entireties.

Maytansinoids are well known in the art and can be synthesized by known techniques or isolated from natural sources. Suitable maytansinoids are disclosed, for example, in U.S. Pat. No. 5,208,020. Exemplary maytansinoid drug moieties include those having a modified aromatic ring, such as: C-19-dechloro (U.S. Pat. No. 4,256,746) prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions. Exemplary maytansinoid drug moieties also include those having modifications such as: C-9-SH, prepared by the reaction of maytansinol with H2S or P2S5 (U.S. Pat. No. 4,424,219); C-14-alkoxymethyl (demethoxy/CH$_2$OR) (U.S. Pat. No. 4,331,598); C-14-hydroxymethyl or acyloxymethyl (CH2OH or CH2OAc), prepared from *Nocardia* (U.S. Pat. No. 4,450,254); C-15-hydroxy/acyloxy, prepared by the conversion of maytansinol by *Streptomyces* (U.S. Pat. No. 4,364,866); C-15-methoxy, isolated from *Trewia nudiflora* (U.S. Pat. Nos. 4,313,946 and 4,315,929); C-18-N-demethyl, prepared by the demethylation of maytansinol by *Streptomyces* (U.S. Pat. Nos. 4,362,663 and 4,322,348); and 4,5-deoxy, prepared by the titanium trichloride/LAH reduction of maytansinol (U.S. Pat. No. 4,371,533). Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

In some aspects, the drug is calicheamicin. The calicheamicin family of antibiotics is capable of producing double-stranded DNA breaks at sub-picomolar concentrations. For the preparation of conjugates of the calicheamicin family see, e.g., U.S. Pat. Nos. 5,712,374, 5,714,586, 5,739,116, 5,767,285, 5,770,701, 5,770,710, 5,773,001, 5,877,296, which are herein incorporated by reference in their entireties. Structural analogues of calicheamicin that can be used include, but are not limited to, γ1I, α2I, α3I, N-acetyl-γ1I, PSAG and θ11 (Hinman et al., Cancer Research 53:3336-3342 (1993), Lode et al., Cancer Research 58:2925-2928 (1998) and the aforementioned U.S. patents to American Cyanamid). In some aspects, the drug is tubulysin. Tubulysins are members of a class of natural products isolated from myxobacterial species (Sasse et al., J. Antibiot. 53:879-885 (2000)). As cytoskeleton interacting agents, tubulysins are mitotic poisons that inhibit tubulin polymerization and lead to cell cycle arrest and apoptosis (Steinmetz et al., Chem. Int. Ed. 43:4888-4892 (2004); Khalil et al., ChemBioChem. 7:678-683 (2006); Kaur et al., Biochem. J. 396: 235-242 (2006)). Tubulysins are extremely potent cytotoxic molecules, exceeding the cell growth inhibition of any clinically relevant traditional chemotherapeutic, e.g., epothilones, paclitaxel, and vinblastine. Furthermore, they are potent against multidrug resistant cell lines (Domling et al., Mol. Diversity 9:141-147 (2005)). These compounds show high cytotoxicity tested against a panel of cancer cell lines with $IC_{50}$ values in the low picomolar range; thus, they are of interest as anticancer therapeutics. See, e.g., Intl. Publ. No. WO2012/019123, which is herein incorporated by reference in its entirety. Tubulysin conjugates are disclosed, e.g., in U.S. Pat. No. 7,776,814.

In some aspects, the drug is a pyrrolobenzodiazepine (PBD). PBDs are relatively small molecules and some have the ability to recognize and covalently bind to specific sequences in the minor groove of DNA and thus exhibit antibiotic/antitumor activity. A number of PBDs and derivatives thereof are known in the art, for example, PBD dimers (e.g., SJG-136 or SG2000), C2-unsaturated PBD dimers, pyrrolobenzodiazepine dimers bearing C2 aryl substitutions (e.g., SG2285), PBD dimer pro-drug that is activated by hydrolysis (e.g., SG2285), and polypyrrole-PBD (e.g., SG2274). PBDs are further described in WO2000/012507, WO2007/039752, WO2005/110423, WO2005/085251, and WO2005/040170, and U.S. Pat. No. 7,612,062, each of which is incorporated by reference herein in its entirety.

In some aspects, the toxin comprises, for example, abrin, brucine, cicutoxin, diphteria toxin, botulinum toxin, shiga toxin, endotoxin, tetanus toxin, pertussis toxin, anthrax toxin, cholera toxin, falcarinol, alpha toxin, geldanamycin, gelonin, lotaustralin, ricin, strychnine, tetrodotoxin, saponin, ribonuclease (RNase), DNase I, *Staphylococcal* enterotoxin-A, pokeweed antiviral protein, *Pseudomonas* exotoxin, *Pseudomonas* endotoxin, or a combination thereof. In other aspects, the toxin comprises, for example, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, mitogellin, restrictocin, phenomycin, neomycin, tricothecenes, or a combination thereof. See, for example, WO93/021232.

In some aspects, the chelating agent is DTPA, EC, DMSA, EDTA, Cy-EDTA, EDTMP, DTPA, CyDTPA, Cy2DTPA, BOPTA, DTPA-MA, DTPA-BA, DTPMP, DOTA, TRITA, TETA, DOTMA, DOTA-MA, HP-DO3A, pNB-DOTA, DOTP, DOTMP, DOTEP, DOTPP, DOTBzP, DOTPME, HEDP, DTTP, an N3S triamidethiol, DADS, MAMA, DADT, an N2S4 diaminetetrathiol, an N2P2 dithiol-bisphosphine, a 6-hydrazinonicotinic acid, a propylene amine oxime, a tetraamine, a cyclam, or a combination thereof.

In one embodiment the drug is an auristatin, a tubulysin or a pyrrolobenzodiazepine (PBD).

In one embodiment the auristatin is MMAE (monomethyl auristatin E) or MMAF (monomethyl auristatin F).

In one embodiment the drug is a maytansinoid, for example N 2'-deacetyl-N 2'-(3-mercapto-1-oxopropyl)-maytansine (DM1), N 2'-deacetyl-N2'-(4-mercapto-1-oxopentyl)-maytansine (DM3) or N 2'-deacetyl-N 2'(4-methyl-4-mercapto-1-oxopentyl)-maytansine (DM4).

Chemotherapeutic agents are drugs but may also legitimately be described as toxins. Toxins which are not registered for use as independent or standalone therapeutic agents are not considered drugs in the context of the present specification.

Examples of radionuclides include $^{3}H$, $^{11}C$, $^{13}N$, $^{15}O$, $^{18}F$, $^{32}P$, $^{33}P$, $^{35}S$, $^{47}Sc$, $^{51}Cr$, $^{54}Mn$, $^{57}Co$, $^{58}Co$, $^{59}Fe$, $^{62}Cu$, $^{65}Zn$, $^{67}Cu$, $^{67}Ga$, $^{68}Ge$, $^{75}Br$, $^{75}Se$, $^{76}Br$, $^{77}Br$, $^{77}As$, $^{80m}Br$, $^{85}Sr$, $^{89}Sr$, $^{90}Y$, $^{95}Ru$, $^{97}Ru$, $^{99}Mo$ and $^{99m}Tc$, $^{103}Pd$, $^{103m}Rh$, $^{103}Ru$, $^{105}R$, $^{105}Ru$, $^{107}Hg$, $^{109}Pd$, $^{109}Pt$, $^{111}Ag$, $^{111}In$, $^{112}In$, $^{113m}In$, $^{113}Sn$, $^{115}In$, $^{117}Sn$, $^{119}Sb$, $^{121m}Te$, $^{121}I$, $^{122m}Te$, $^{125m}Te$, $^{125}I$, $^{126}I$, $^{131}I$, $^{133}I$, $^{133}Xe$, $^{140}La$, $^{142}Pr$, $^{143}Pr$, $^{149}Pm$, $^{152}Dy$, $^{153}Sm$, $^{153}Gd$, $^{159}Gd$, $^{161}Ho$, $^{161}Tb$, $^{165}Tm$, $^{166}Dy$, $^{166}Ho$, $^{167}Tm$, $^{168}Tm$, $^{169}Er$, $^{169}Yb$, $^{175}Yb$, $^{177}Lu$, $^{186}Re$, $^{188}Re$, $^{188}W$, $^{189m}Os$, $^{189}Re$, $^{192}Ir$, $^{194}Ir$, $^{197}Pt$, $^{198}Au$, $^{199}Au$, $^{201}Tl$, $^{203}Hg$, $^{211}At$, $^{211}Bi$, $^{211}Pb$, $^{212}Pb$, $^{212}Bi$, $^{213}Bi$, $^{215}Po$, $^{217}At$, $^{219}Rn$, $^{221}Fr$, $^{223}Ra$, $^{224}Ac$, $^{225}Ac$, $^{225}Fm$, $^{252}Cf$ and a combination thereof.

In one embodiment the radionuclide is selected from the group comprising or consisting of chromium ($^{51}Cr$), cobalt ($^{57}Co$), fluorine ($^{18}F$), gadolinium ($^{153}Gd$, $^{159}Gd$), germanium ($^{68}Ge$), holmium ($^{166}Ho$), indium ($^{115}In$, $^{113}In$, $^{112}In$, $^{111}In$), iodine ($^{131}I$, $^{125}I$, $^{123}$, $^{121}I$) lanthanum ($^{140}La$), lutetium ($^{177}Lu$), manganese ($^{54}Mn$), molybdenum ($^{99}Mo$), palladium ($^{103}Pd$), phosphorous ($^{32}P$), praseodymium ($^{142}Pr$), promethium ($^{149}Pm$), rhenium ($^{186}Re$, $^{188}Re$), rhodium ($^{105}Rh$), ruthenium ($^{97}Ru$), samarium ($^{153}Sm$), scandium ($^{47}Sc$), selenium ($^{75}Se$), strontium ($^{85}Sr$), sulfur ($^{35}S$), technetium ($^{99}Tc$), thallium ($^{201}Tl$), tin ($^{113}Sn$, $^{117}Sn$), tritium ($^{3}H$), xenon ($^{133}Xe$), ytterbium ($^{169}Yb$, $^{175}Yb$) yttrium ($^{90}Y$), zinc ($^{65}Zn$), or a combination thereof.

In one embodiment the radionuclide is attached to the conjugate compound of the present disclosure by a chelating agent.

In one embodiment the payload is a serum half-life extender, for example comprising albumin, albumin binding polypeptide, PAS, the β subunit of the C-terminal peptide (CTP) of human chorionic gonadotropin, polyethylene glycol (PEG), hydroxyethyl starch (HES), XTEN, albumin-binding small molecules, or a combination thereof.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific naturally occurring polymers include lactose, hyaluronic acid, heparan sulphate, chondroitin sulphate, alginate, cellulose amylose, dextran, glycogen or derivatives thereof.

In some embodiments, the polymer is polyethylene glycol (PEG), branched PEG, polysialic acid (PSA), hydroxyalkyl starch (HAS), hydroxylethyl starch (HES), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG) polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(l-hydroxymethylethylene hydroxymethylformal) (PHF), 2-methacryloyloxy-2'-ethylt-rimethylammoniumphosphate (MPC). In some embodiments, the polymer is polyethylene glycol. In one embodiment of the invention, the polyethylene glycol has a molecular weight range of 300 to 10,000,000, 500 to 100,000, 1000 to 50,000, 1500 to 30,000, 2,000 to 20,000 Da, 3,000 to 5,000 Da, and 4,000 to 5,000 Da. In other embodiments, the polyethylene glycol has a molecular weight of about 1,000 Da, about 1,500 Da, about 2,000 Da, about 3,000 Da, about 4,000 Da, about 5,000 Da, about 10,000 Da, or about 20,000 Da.

In one embodiment payload comprises a visualization label. Visualization labels include, without limitation, a chromophore, a fluorophore, a fluorescent protein, a phosphorescent dye, a tandem dye, a particle, a hapten, an enzyme, a radioisotope, or a combination thereof.

In one embodiment the visualization label is a visualization peptide. In some aspects, the visualization peptide enables visualization or localization of the conjugate compound in vitro, in vivo, ex vivo, or any combination thereof. In some aspects, the visualization peptide is, for example, a biotin acceptor peptide, a lipoic acid acceptor peptide, a fluorescent protein, a cysteine-containing peptide for ligation of a biarsenical dye or for conjugating metastable technetium, a peptide for conjugating europium clathrates for fluorescence resonance energy transfer (FRET)-based proximity assays, or any combination thereof. In some aspects, the fluorescent protein is, for example, green fluorescent protein (GFP), red fluorescent protein (RFP), yellow fluorescent protein (YFP), enhanced green fluorescent protein (EGFP), enhanced yellow fluorescent protein (EYFP), or any combination thereof. In some aspects, the fluorescent protein is a phycobiliprotein or a derivative thereof.

Fluorescent proteins, especially phycobiliprotein, are useful for creating tandem dye labeled labeling reagents. These tandem dyes comprise a fluorescent protein and a fluorophore for the purposes of obtaining a larger stokes shift where the emission spectra is farther shifted from the wavelength of the fluorescent protein's absorption spectra. This can be effective for detecting a low quantity of a target in a sample where the emitted fluorescent light is maximally optimized, in other words little to none of the emitted light is reabsorbed by the fluorescent protein. For this to work, the fluorescent protein and fluorophore function as an energy transfer pair where the fluorescent protein emits at the wavelength that the fluorophore absorbs at and the fluorophore then emits at a wavelength farther from the fluorescent proteins than could have been obtained with only the fluorescent protein. A functional combination can be phycobiliproteins and sulforhodamine fluorophores, or sulfonated cyanine fluorophores as known in the art. The fluorophore sometimes functions as the energy donor and the fluorescent protein is the energy acceptor.

In other aspects, the biarsenical dye is employed as the payload is 4',5'-bis(1,3,2-dithioarsolan-2-yl)fluorescein (FlAsH). In some aspects, the biotin acceptor peptide facilitates conjugation of avidin- and streptavidin-based reagents. In some aspects, the lipoic acid acceptor peptide facilitates conjugation of thiol-reactive probes to bound lipoic acid or direct ligation of fluorescent lipoic acid analogs.

In one embodiment the payload or the polypeptide comprises a fluorescent tag. In some aspects, the fluorescent tag comprises, for example, a fluorescein-type dye, a rhodamine-type dye, dansyl-type dye, a lissamine-type dye, a cyanine-type dye, a phycoerythrin-type dye, a Texas Red-type dye, or any combination thereof. Fluorophores suitable for conjugation to the cysteine-engineered antibodies or antigen-binding fragments thereof disclosed herein include, without limitation; a pyrene (including any of the corresponding derivative compounds), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds), a carbocyanine (including any corresponding compounds), a carbostyryl, a porphyrin, a salicylate, an anthranilate, an azulene, a perylene, a pyridine, a quinoline, a borapolyazaindacene (including any corresponding compounds), a xanthene (including any corresponding compounds), an oxazine (including any corresponding compounds) or a benzoxazine, a carbazine (including any corresponding compounds), a phenalenone, a coumarin (including an corresponding compounds disclosed), a benzofuran (including an corresponding compounds) and benzphenalenone (including any corresponding compounds) and derivatives thereof. As used herein, oxazines include resorufins (including any corresponding compounds), aminooxazinones, diaminooxazines, and their benzo-substituted analogs, or any combination thereof.

In certain aspects, the fluorophores include, for example, xanthene (rhodol, rhodamine, fluorescein and derivatives thereof) coumarin, cyanine, pyrene, oxazine, borapolyazaindacene, or any combination thereof. In some embodiments, such fluorophores are, for example, sulfonated xanthenes, fluorinated xanthenes, sulfonated coumarins, fluorinated coumarins, sulfonated cyanines, or any combination thereof. Also included are dyes sold under the tradenames, and generally known as, ALEXA FLUOR®, DYLIGHT®, CY DYES®, BODIPY®, OREGON GREEN®, PACIFIC BLUE®, IRDYES®, FAM®, FITC®, and ROX®.

The choice of the fluorophore attached via a linker, which will determine the absorption and fluorescence emission properties of the final compound. Physical properties of a fluorophore label that can be used include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. In certain aspects, the fluorophore has an absorption maximum at wavelengths greater than 480 nm. In some aspects, the fluorophore absorbs at or near 488 nm to 514 nm (particularly suitable for excitation by the output of the argon-ion laser excitation source) or near 546 nm (particularly suitable for excitation by a mercury arc lamp). In some aspects, a fluorophore can emit in the NIR (near infrared region) for tissue or whole organism applications. Other desirable properties of the fluorescent label can include cell permeability and low toxicity, for example if labeling of the antibody is to be performed in a cell or an organism (e.g., a living animal).

In one embodiment the polypeptide or the payload comprises a capture tag. In some aspects, the capture tag is biotin or a His6 tag. Biotin is useful because it can function in an enzyme system to further amplify a detectable signal, and it can also function as a tag to be used in affinity chromatography for isolation purposes. For detection purposes, an enzyme conjugate that has affinity for biotin can be used, such as avidin-HRP.

Subsequently a peroxidase substrate can be added to produce a detectable signal. In addition to biotin, other haptens can be used, including hormones, naturally occurring and synthetic drugs, pollutants, allergens, effector molecules, growth factors, chemokines, cytokines, lymphokines, amino acids, peptides, chemical intermediates, nucleotides and the like.

In one embodiment the payload comprises an enzyme. Enzymes are effective labels because amplification of the detectable signal can be obtained resulting in increased assay sensitivity. The enzyme itself often does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. The enzyme substrate is selected to yield the measurable product, e.g., colorimetric, fluorescent or chemiluminescence. Such substrates are extensively used in the art and are known in the art.

In some embodiments, colorimetric or fluorogenic substrate and enzyme combination uses oxidoreductases such as horseradish peroxidase and a substrate such as 3,3'-diaminobenzidine (DAB) and 3-amino-9-ethylcarbazole (AEC), which yield a distinguishing color (brown and red, respectively). Other colorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants and reduced dihydroxanthenes, including dihydrofluoresceins and dihydrorhodamines including dihydrorhodamine 123.

The present disclosure extends to employing peroxidase substrates that are tyramides that represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

The present disclosure extends to employing a colorimetric (and in some cases fluorogenic) substrate and enzyme combination sometimes uses a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912) fluorescein diphosphate, 3-O-methylfluorescein phosphate, resorufin phosphate, 9H-(1, 3-dichloro-9,9-dimethylacridin-2-one-7-yl) phosphate (DDAO phosphate), or ELF 97, ELF 39 or related phosphates.

The disclosure also extends to a payload comprising a glycosidase, in particular beta-galactosidase, beta-glucuronidase and beta-glucosidase, are additional suitable enzymes. Appropriate colorimetric substrates include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. In some embodiments, fluorogenic substrates include resorufin beta-D-galactopyranoside, fluorescein digalactoside (FDG), fluorescein diglucuronide and their structural variants, 4-methylumbelliferyl beta-D-galactopyranoside, carboxyumbelliferyl beta-D-galactopyranoside and fluorinated coumarin beta-D-galactopyranosides. Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are useful for incorporation into molecules of the present disclosure. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters may also be useful.

The nucleic acid employed maybe selected from the group consisting of DNA, RNA, short interfering RNA (siRNA), microRNA, hairpin or nucleic acid mimetics such as peptide nucleic acids. In certain aspects, the conjugated nucleic acid is at least 10, at least 20, at least 30, at least 40, at least 50, at least 60 at least 100, at least 200, at least 500, at least 1000, at least 5000, or more base pairs. The conjugated nucleic acid can be single stranded. In various aspects, the conjugated nucleic acid can be double stranded. In some aspects, the conjugated nucleic acid encodes an open reading frame. In some aspects, the open reading frame encoded by the conjugated nucleic acid corresponds to an apoptosis inducing protein, a viral protein, an enzyme, or a tumor suppressor protein. Techniques for delivery of such nucleic acids to cells are known in the art.

In one embodiment the payload conjugated through a reactive sugar to a glycan in an antibody of the present disclosure is as shown below:

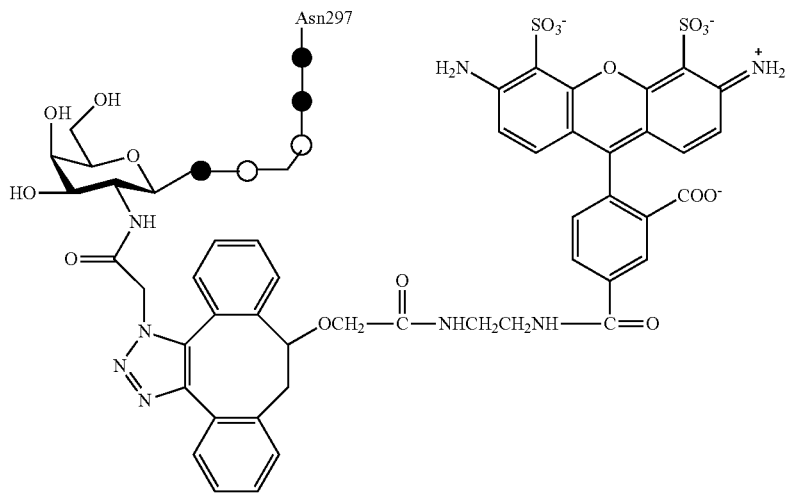

wherein Asn297 represents an Asn residue at position 297 in an antibody.

In one embodiment the molecules prepared are stable, or example physically, chemically and/or thermally stable. Evidence of physically instability is, for example aggregation, which can be measured by routine techniques, such as size exclusion chromatography. Evidence of chemical instability is, for example degradation or disintegration of the molecule, such as disconnection of the payload. Evidence of thermal instability is, for example denaturing.

Other Definitions

As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects, which can be had by reference to the specification as a whole. Accordingly, the terms defined immediately below are more fully defined by reference to the specification in its entirety.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The term "subject" refers to any animal (e.g., a mammal), including, but not limited to humans, non-human primates, rodents, and the like, which is to be the recipient of a particular treatment. Typically, the terms "subject" and "patient" can be used interchangeably in reference to a human subject.

The term "pharmaceutical composition" refers to a preparation which is in such form as to permit the biological activity of the active ingredient (e.g., an antibody conjugate disclosed herein) to be effective, and which contains no additional components which are unacceptably toxic to a subject to which the composition would be administered. Such composition may comprise one or more pharmaceutically acceptable excipients. Such composition can be sterile.

An "effective amount" of a conjugate compound as disclosed herein is an amount sufficient to carry out a specifically stated purpose. An "effective amount" can be determined empirically and in a routine manner, in relation to the stated purpose.

The term "therapeutically effective amount" refers to an amount of conjugate compound disclosed herein or other drug effective to "treat" a disease or disorder in a subject or mammal.

The word "label" when used herein refers to a detectable compound or composition which is conjugated directly or indirectly to an antibody or fragment thereof disclosed herein (e.g., a glycan engineered antibody or fragment thereof,) so as to generate a "labeled" conjugate compound. The label can be detectable by itself (e.g., radioisotope labels or fluorescent labels) or, in the case of an enzymatic label, can catalyze chemical alteration of a substrate compound or composition that is detectable.

Terms such as "treating" or "treatment" or "to treat" refer to both (1) therapeutic measures that cure, slow down, ameliorate symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for a disease or condition, for example, cancer, according to the methods of the present disclosure if the patient shows, e.g., total, partial, or transient remission of the disease or condition, for example, a certain type of cancer.

The terms "polynucleotide" and "nucleic acid" are used interchangeably herein and refer to polymers of nucleotides of any length, including DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs.

The term 'oligonucleotide' as employed herein is intended to refer to short polynucleotides, for example 100 base in length or less, such as 50 bases or less.

As used herein, the term "vector" refers to a construct, which is capable of delivering, and in some aspects, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, the term "comprising" in context of the present specification should be interpreted as "including".

"Employed in the present disclosure" as used herein refers to employed in the method disclosed herein, employed in the molecules including intermediates disclosed herein or both, as appropriate to the context of the term used.

It is understood that wherever aspects are described herein with the language "comprising," otherwise analogous aspects described in terms of "consisting of" and/or "consisting essentially of" are also provided.

Any positive embodiment or combination thereof described herein may be the basis of a negative exclusion i.e. a disclaimer.

Compositions

The present disclosure extends to compositions comprising an antibody molecule described herein (for example comprising a payload), in particular a pharmaceutical composition (or diagnostic composition) comprising a molecule of the present disclosure and pharmaceutical excipient, diluent or carrier.

The composition will usually be supplied as part of a sterile, pharmaceutical composition that will normally include a pharmaceutically acceptable carrier.

The disclosure also extends to processes of preparing said compositions, for example preparation of a pharmaceutical or diagnostic composition comprising adding and mixing a molecule of the present disclosure together with one or more of a pharmaceutically acceptable excipient, diluent or carrier.

The antibody of the disclosure may be the sole active ingredient in the pharmaceutical or diagnostic composition or may be accompanied by other active ingredients.

The pharmaceutical compositions suitably comprise a therapeutically effective amount of a molecule according to the disclosure. The term "therapeutically effective amount" as used herein refers to an amount of a therapeutic agent needed to treat, ameliorate or prevent a targeted disease or condition, or to exhibit a detectable therapeutic or preventative effect. The therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. Pharmaceutical compositions may be conveniently presented in unit dose forms containing a predetermined amount of an active agent of the invention per dose. The actual dose at which a molecule of the present disclosure is administered depends on the nature of the condition to be treated, for example the extent of the disease/inflammation present and on whether the molecule is being used prophylactically or to treat an existing condition.

Compositions may be administered individually to a patient or may be administered in combination (e.g. simultaneously, sequentially or separately) with other agents, drugs or hormones.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the molecule of the disclosure may be in dry form, for reconstitution before use with an appropriate sterile liquid.

Suitably in formulations according to the present disclosure, the pH of the final formulation is not similar to the value of the isoelectric point of the antibody, for example if the pH of the formulation is 7 then a pI of from 8-9 or above may be appropriate. Whilst not wishing to be bound by theory it is thought that this may ultimately provide a final formulation with improved stability, for example the antibody remains in solution.

The pharmaceutical compositions of this disclosure may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles, such as isotonic solution, prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion or tumor. Dosage treatment may be a single dose schedule or a multiple dose schedule.

It will be appreciated that the composition comprises a polypeptide (i.e. an antibody or binding fragment thereof) and as such, it may be susceptible to degradation in the gastrointestinal tract. Thus, if the composition is to be administered by a route using the gastrointestinal tract, the composition will need to contain agents which protect the polypeptide from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

Treatment

The present disclosure also extends to methods of treating a patient in need thereof by administering a therapeutically effective amount of a molecule according to the present disclosure or a composition, such as pharmaceutical composition comprising the same.

In one embodiment there is provided a molecule of the present disclosure or a composition comprising same, for use in treatment, in particular for use of the treatment of a disease or condition described herein, such as cancer.

In one embodiment is provided use of a molecule of the present disclosure or a composition comprising the same in the manufacture of a medicament for treating a condition or disease described herein, such as cancer.

Thus the molecules of the present invention are useful in the treatment and/or prophylaxis of a pathological condition.

Thus there is provided a molecule according to the present invention for use in treatment, by administering a therapeutically effective amount thereof, for example in a pharmaceutical formulation. In one embodiment the molecule according to the disclosure is administered topically to the lungs, for example by inhalation.

The antibodies provided by the present invention are useful in the treatment of diseases or disorders including inflammatory diseases and disorders, immune disease and disorders, fibrotic disorders and cancers.

The term "inflammatory disease" or "disorder" and "immune disease or disorder" includes rheumatoid arthritis, psoriatic arthritis, still's disease, Muckle Wells disease, psoriasis, Crohn's disease, ulcerative colitis, SLE (Systemic Lupus Erythematosus), asthma, allergic rhinitis, atopic dermatitis, multiple sclerosis, vasculitis, Type I diabetes mellitus, transplantation and graft-versus-host disease.

The term "fibrotic disorder" includes idiopathic pulmonary fibrosis (IPF), systemic sclerosis (or scleroderma), kidney fibrosis, diabetic nephropathy, IgA nephropathy, hypertension, end-stage renal disease, peritoneal fibrosis (continuous ambulatory peritoneal dialysis), liver cirrhosis, age-related macular degeneration (ARMD), retinopathy, cardiac reactive fibrosis, scarring, keloids, burns, skin ulcers, angioplasty, coronary bypass surgery, arthroplasty and cataract surgery.

The term "cancer" includes a malignant new growth that arises from epithelium, found in skin or, more commonly, the lining of body organs, for example: breast, ovary, prostate, colon, lung, kidney, pancreas, stomach, bladder or bowel. Cancers tend to infiltrate into adjacent tissue and spread (metastasise) to distant organs, for example: to bone, liver, lung or the brain.

In one embodiment, the treatment is administered for a primary cancer. In one embodiment the treatment is for a metastatic cancer. In one embodiment the treatment is for a combination of primary cancer and metastatic cancer.

The subjects to be treated can be animals. However, in one or more embodiments the compositions are adapted for administration to human subjects.

FIGURES

FIGS. 1A & 1B (SEQ ID NO: 1) are a diagrammatic representation of various glycans.

FIG. 2 is a diagrammatic representation of the altered N-glycans, mucin O-glycans, O-fructose and O-mannose glycans in certain CHO glycosylation mutants. The loss or reduction of a particular sugar at a particular position is indicated by a minus (−) sign, whereas gain of a sugar residue is indicated by a plus (+) sign. Asparagine, threonine, or serine residues bearing the different glycans are indicated by their single letter amino acid code. Sugar symbols: grey triangle—fructose, grey circle—mannose, white circle—galactose; black square—N-acetylglucosamine, white square—N-acetylgalactosamine, grey trapezoid—sialic acid.

FIG. 6A shows a schematic representation and conditions for UDP-keto Gal transfer to G0F form glycans on antibodies of Example 4.

FIG. 6B shows the mass spectrum of a G0F antibody before transfer of the reactive sugar Keto-Gal FIG. 6C shows the mass spectrum of the antibody of FIG. 6B after transfer of the reactive sugar Keto-Gal.

FIG. 9 shows the SDS PAGE of the antibody conjugated to DBCO-Fluor® 488. The N-glycan of antibody in the conjugate was expressed in LEC8 cells is in G0F form, with GalNAz transferred thereto by mutant GalT (Y289L) followed by click chemistry to add DBCO-Fluor® 488.

FIG. 11A shows the impact of the concentration of the mutant GalT enzyme on the molecular ratio obtained.

FIG. 11B shows the impact of the concentration of the reactive sugar reagent UDP-GalNAz on the molecule ratio obtained.

FIG. 12 shows the impact of the equivalents of payload on the molecular ratio obtained.

EXAMPLES

Synthesis of Sugars

Example 1a Chemical Synthesis of UDP-GalNAz

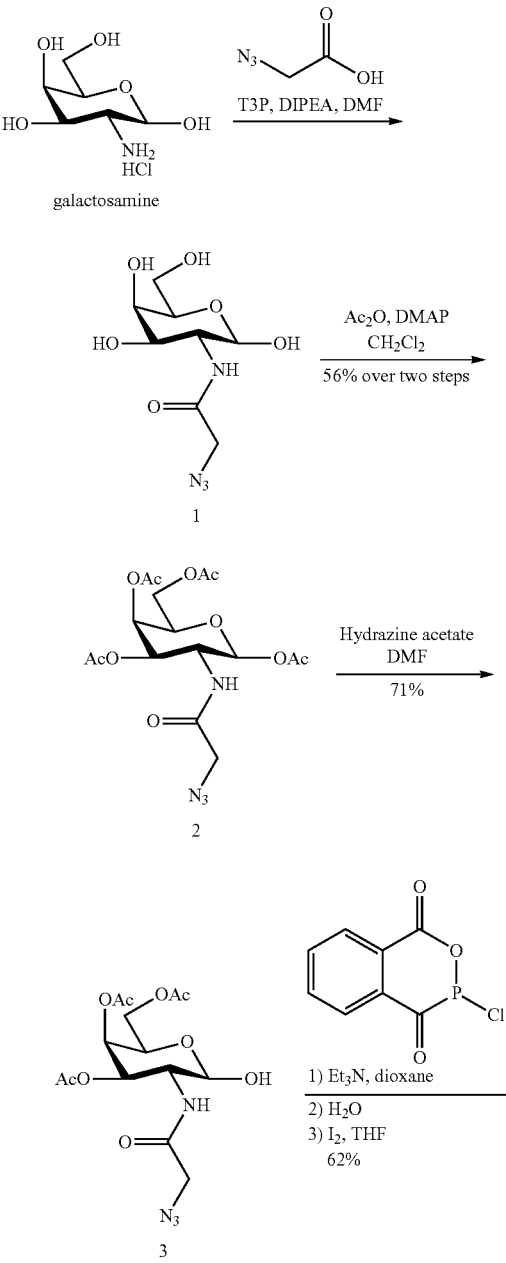

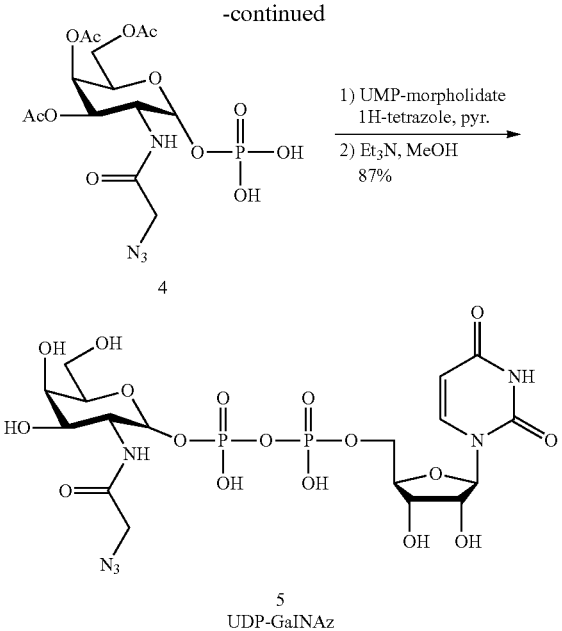

4

5
UDP-GalNAz

Generation of G0F Glycosylated Antibodies by Two Alternative Methods

Figure 2:
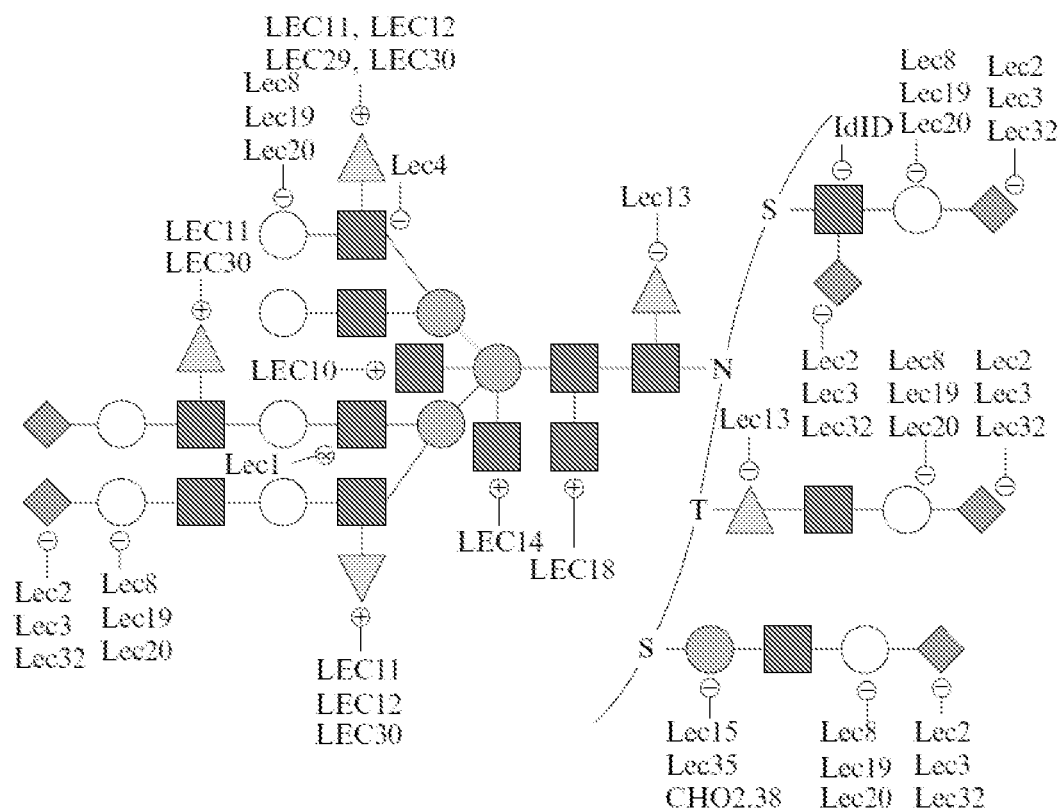
Figure 3:
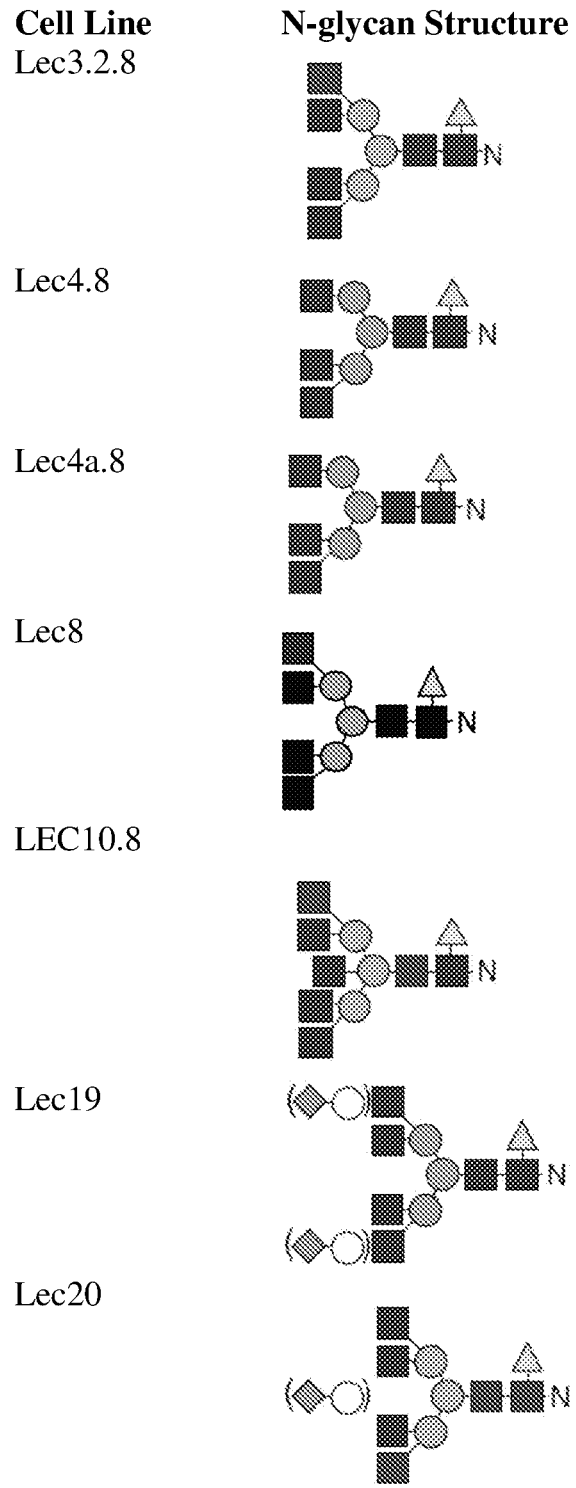
FIG. 3 shows the structure of N-glycan an proteins synthesised by various specific Lec cell lines.
Figure 4:
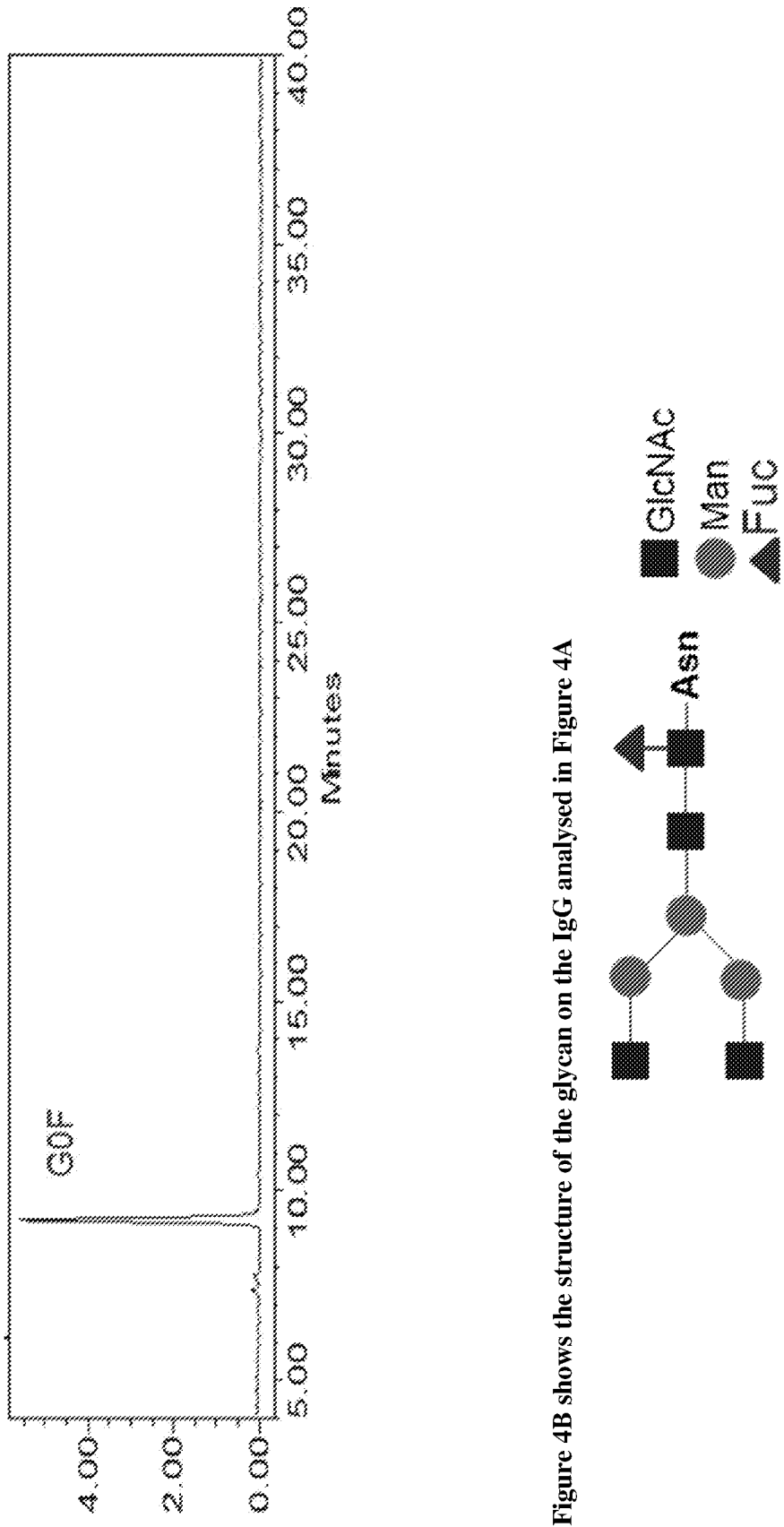
FIG. 4A shows HPLC analysis of an of an IgG antibody expressed in CHO-LEC8 cells as G0F glycan form. The G0F glycan fragment is shown in FIG. 4B.

Example 2 CHO-LEC8 Host Cells are Capable of Expressing a G0F N-Glycoform of an IgG Antibody Suspension adapted CHO LEC8 cells were maintained in M30V2 (in house medium) growth medium in 2 L vent capped shake flasks in an orbital shaker at 37° C., 8% $CO_2$, 80% humidity, and 120 rpm (Infors USA, Laurel, Md.). Cells were seeded at $6 \times 10^5$ cells/ml the day before transfection and adjusted to $1 \times 10^6$ cells/mL to maintain cells in log phase on the day of transfection. PEImax (Polysciences) and plasmid DNA bearing antibody of interest were diluted into 150 mM NaCl at the final concentration of 240 µg/ml and 60 µg/ml, respectively. Equal volume of diluted PEI was added into the diluted plasmid DNA. After 1 minute incubation at room temperature, the PEI/DNA mixture was added to the CHO-LEC8 cells at the final concentration of 1 µg per ml of culture volume. Cell culture were fed with 0.8% of feed medium F09 (in house medium) and 0.05% of feed medium F10 (in house medium) every other day from the $3^{rd}$ day post transfection. The cell culture were harvested at day 10 or 14 post transfection and the antibodies were purified by affinity chromatography using protein A column. HPLC analysis of the antibodies produced are shown in FIG. 4A. FIG. 4A shows only G0F was found in antibody expressed in CHO-LEC8 cells. The N-glycan of antibodies generated from other mammalian cells (e.g., CHO and HEK293) are the mixture of N-glycan with the majority of them in G0F, G1F, and G2F.

Figure 5:
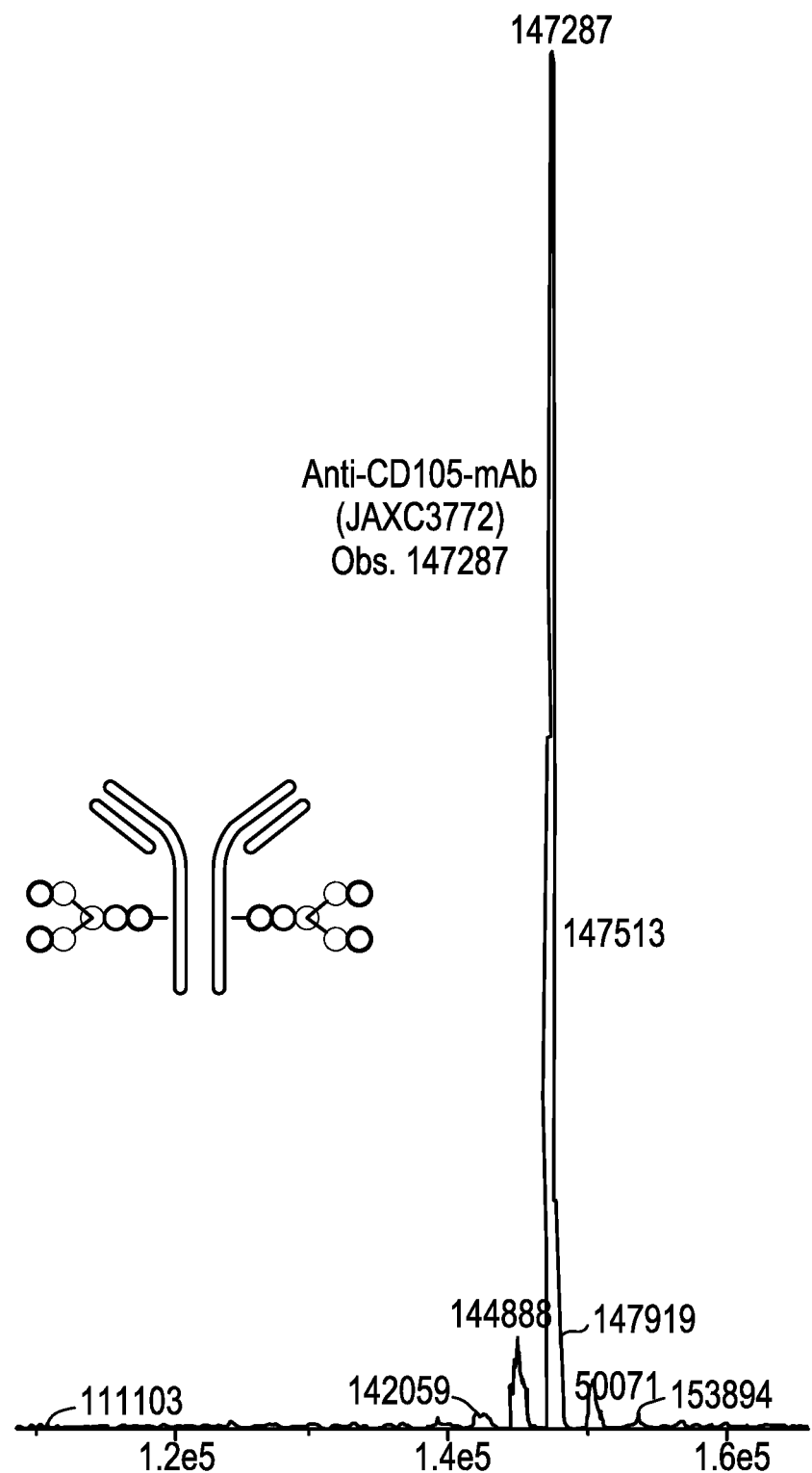
FIG. 5 shows a mass spec analysis of the G0F N-glycoform of an anti CD105 antibody.

Example 3 the Substrate from Example 3 Treated with GalT(Y289L) to Transfer GalNAz from UDP-GalNAz Prepared in Example 1a The mutant Y289L GalT (final concentration, 0.20 mg/mL, 4.5 µM) was dissolved in 25 mM Tris buffer, pH 7.2 containing 150 mM NaCl and 5 mM MnCl2. UDP-GalNAz and antibody were added to final concentrations of 0.6 mM and 1.0 mg/mL (6.7 µM), respectively. Reaction was incubated at 30° C. for 16 h. The excess of reagent was removed by washing with Tris buffer using a 50 kDa cutoff spin filter (Amicon® Ultra-4 centrifugal filter), after which an aliquot of the azide-modified antibody was removed for product analysis by LC-ESI-MS (FIG. 5A). The antibody concentration was determined by the bicinchoninic acid assay (Pierce™ BCA protein assay), and diluted by Tris buffer (25 mM Tris-Cl, 150 mM NaCl, pH 7.2) to 1 mg/ml concentration.

Figure 7A:
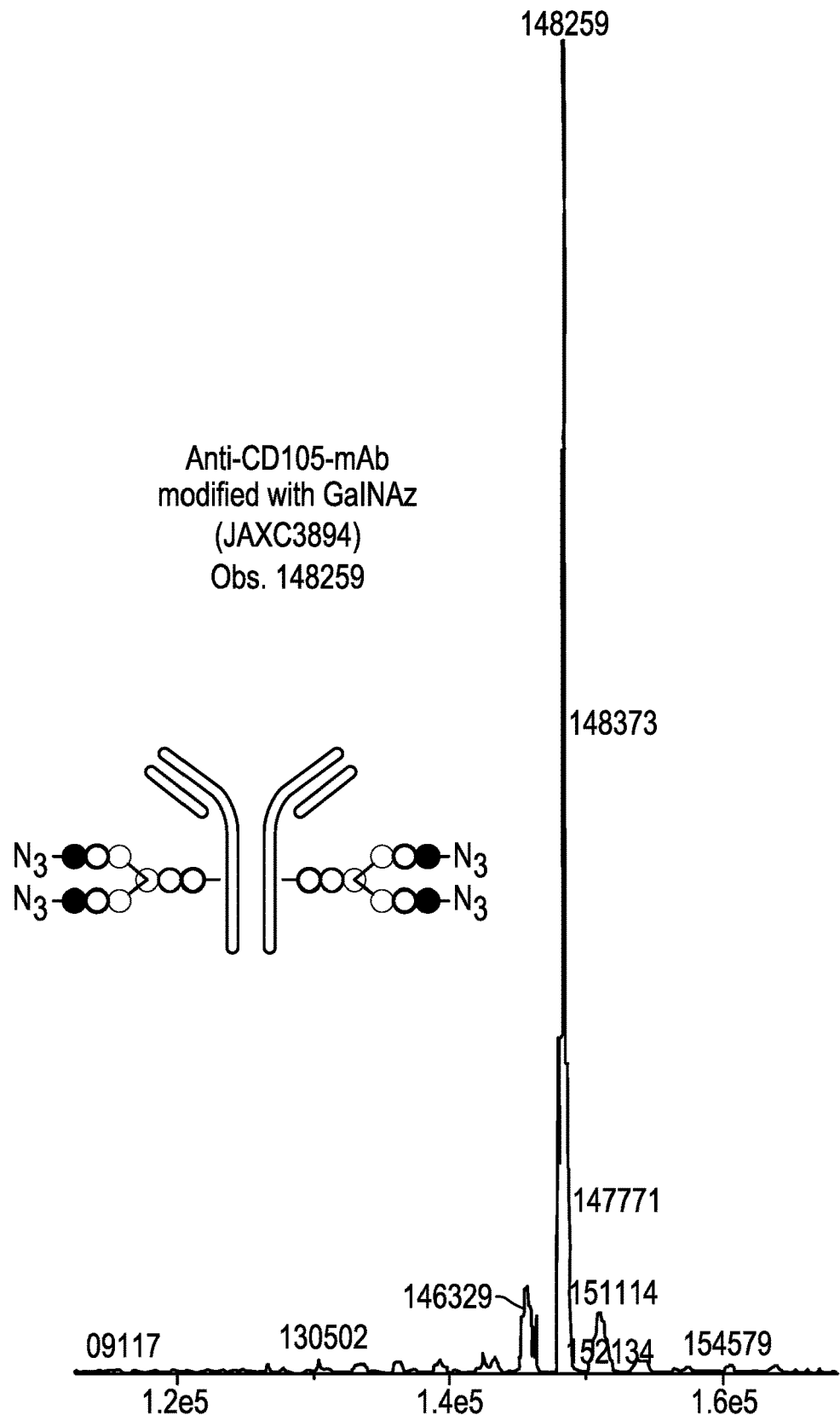
FIG. 7A shows a mass spectrum for antibody CD105 modified with GalNAz.
Figure 7B:
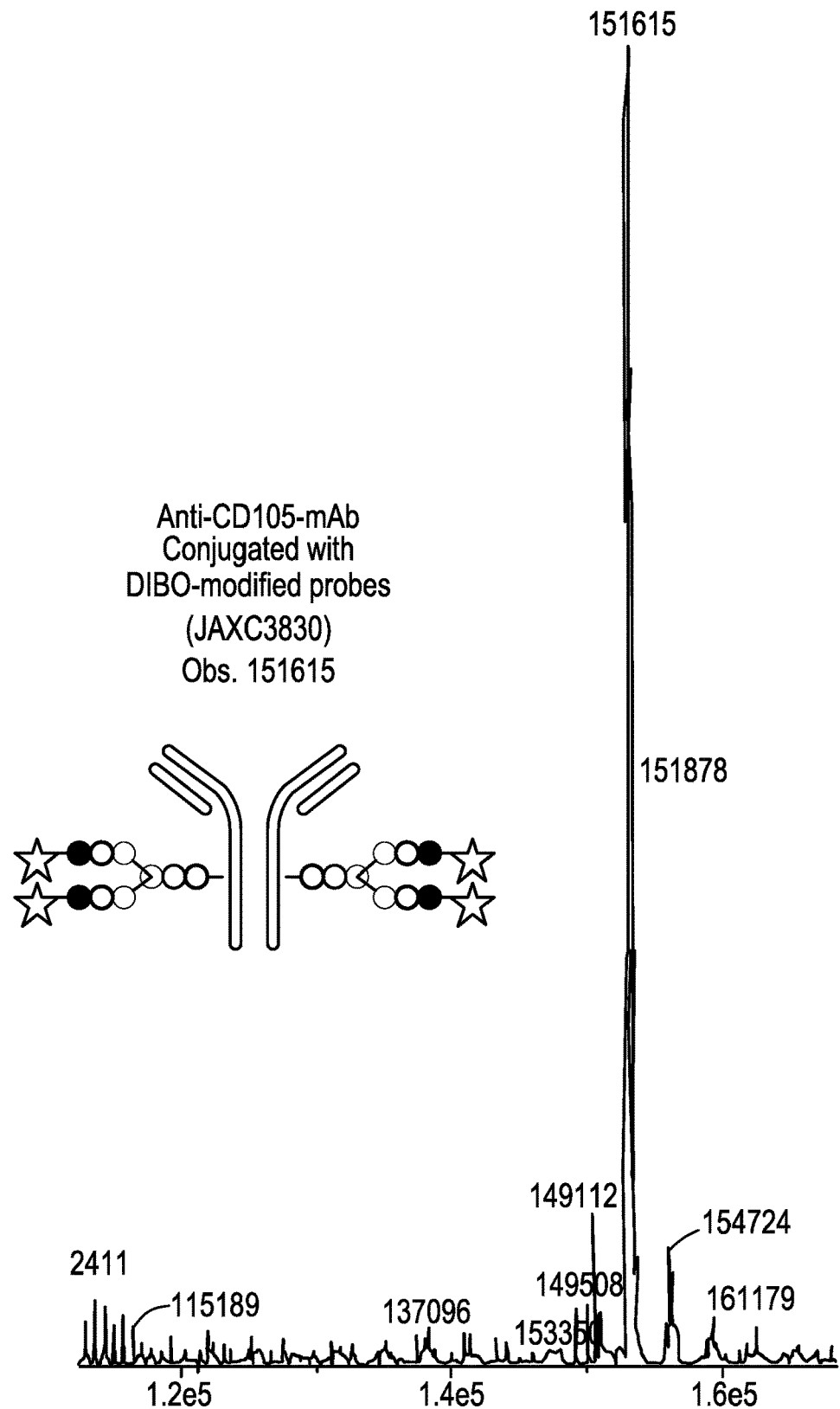
FIG. 7B shows the mass spectrum of antibody CD105 from FIG. 5A after conjugation to DIBO.
Figure 8:
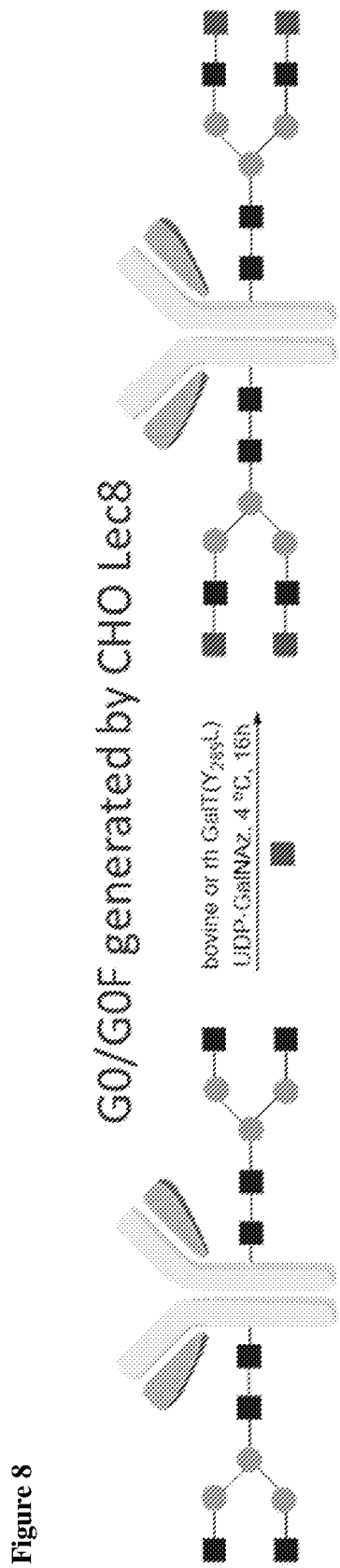
FIG. 8 shows a schematic representation of the G0F form antibodies expressed from LEC8 cells and reacted with UDP-GalNAz.
Figure 10A:
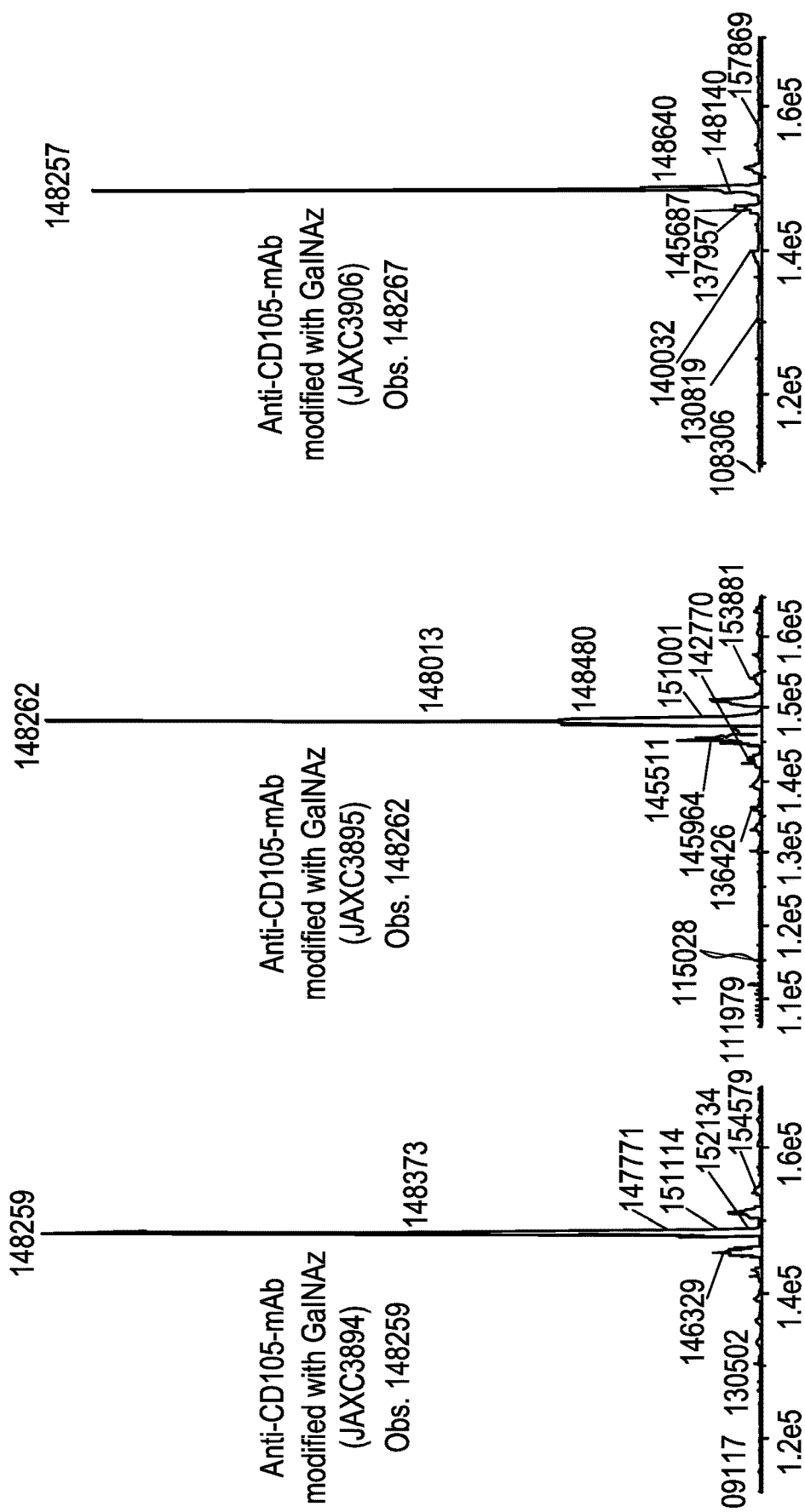
FIG. 10A shows a mass spec analysis of an antibody expressed in LEC8 cells with an reactive sugar GalNAz which has been transferred thereto by mutant GalT.
Figure 10B:
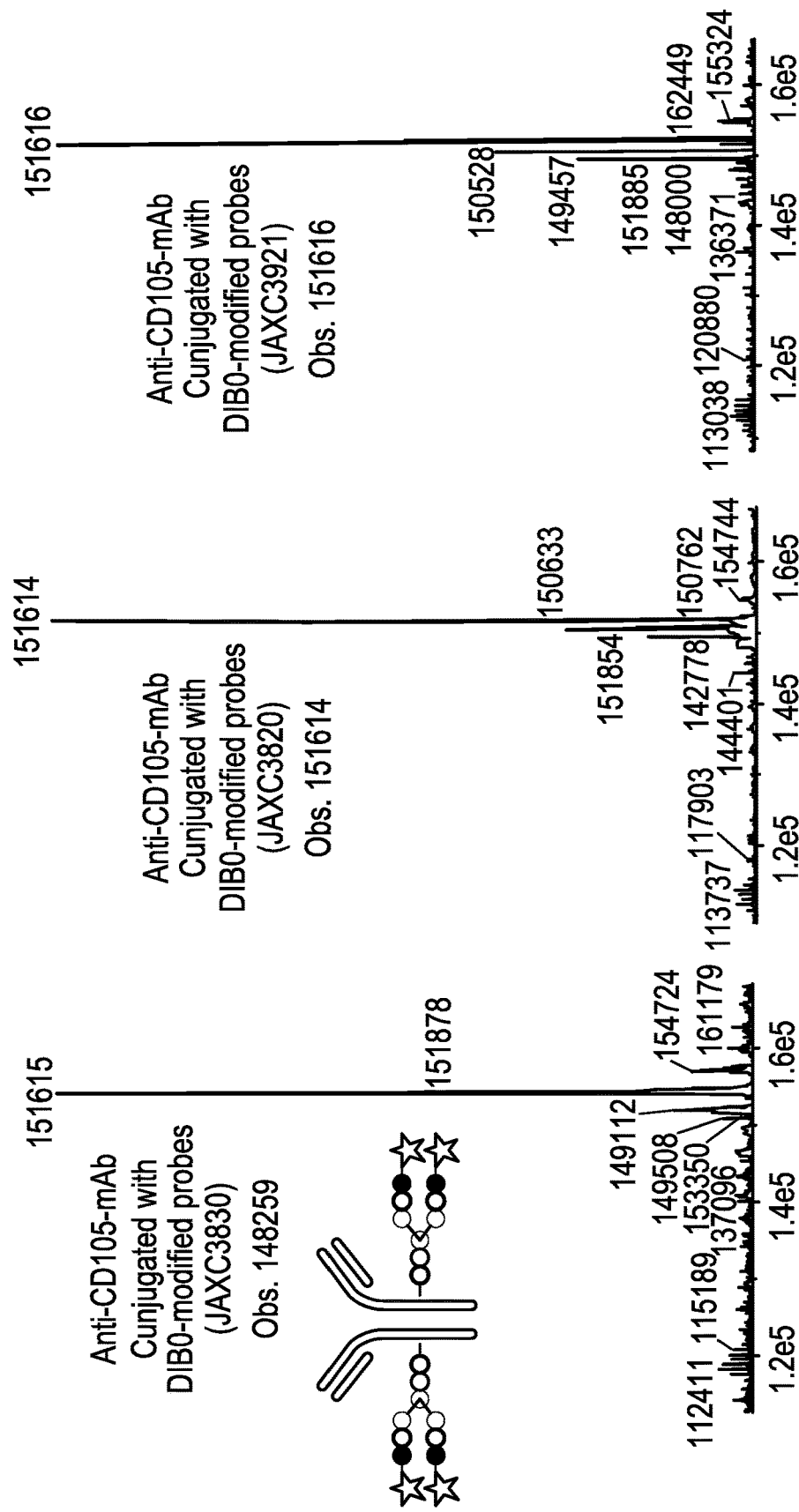
FIG. 10B is the antibody of FIG. 10A conjugated to DBCO-Fluor® 488 through the reactive sugar by click chemistry.

MALDI TOF analysis for the antibody GalNAz product obtained is shown in FIG. 7A. The MALDI TOF analyse after conjugation to a DIBO-modified probe is provided in FIG. 7B wherein the glycan terminating in a "star" represent a glycan conjugated to a payload. The LCMS data for the conjugated molecule is shown below:

$$\frac{151615 - 147287}{1079.2199} = 4.01$$

This data supports the conclusion that 4 payload molecules are conjugated to the antibody.

Example 4 the Substrate from Example 2 Treated with GalT(Y289L) to Transfer Keto-Gal from UDP-Keto Gal The G0F antibody, human GalT (Y285L) mutant, and UDP-2-Keto-Gal 1 were added into 30 mM Tris-HCl buffer (pH 8.0) containing 25 mM of MnCl to the final concentration of 3.4 mM, 10 mM, and 4 mM, respectively. The reaction mixture was incubated at 30 C for 16h in the dark. The excess of reagent was removed by dialyzing in PBS 1×. The product was confirmed by reduced MS the results of which are shown in FIG. 6A.

Example 5 Antibody of Example 3 Conjugated to DIBO-Alexa Fluor®488 Using Click Chemistry The DIBO-Alexa Fluor®488 (final concentration, 19.8 µM) was added to the GalNaz modified antibody (final concentration, 0.5 mg/mL, 3.3 µM) in Tris buffer (25 mM Tris-Cl, 150 mM NaCl, pH 7.2). The reaction mixture was incubated at 25° C. for 16 h. The excess of reagent was removed by washing with Tris buffer using a 50 kDa cutoff spin filter (Amicon® Ultra-4 centrifugal filter), after which an aliquot of the DIBO-Alexa Fluor®488 modified antibody was removed for product analysis by LC-ESI-MS.

Example 6

Using the methodology described in Example 3 optimised concentration of the mutant GalT employed in the enzymatic transfer of the reactive sugar GalNAz were investigated. The reaction was carried out with antibody at the concentration of 6.704, UDP-GalNAz at a concentration of 0.6 mM. $MnCl_2$ at 5 mM, NaCl at 150 mM, and Tris buffer at 25 mM (pH7.2). The enzyme concentration tested was 3.5, 4.5 and 604. Mutant GalT at 4.5 µM is chosen for further experiments since it's sufficient to conjugate 4 GalNaz per antibody.

The ratio was calculated using the following formula:

$$\Delta MW(\text{Unit}) = MW(\text{UDP\_GlaNAz}) - MW(\text{OH}) - MW(\text{H}) = 245.0886$$

$$\text{Ratio}(GlaNAz \text{ per } mAb) = \frac{MW(\text{IgG\_GlaNAz}) - MW(IgG)}{245.0886}$$

The results are shown in FIG. 11A.

The optimised concentration of UDP-GalNAz concentration for enzymatic transfer of the reactive sugar GalNAz was investigated. The antibody concentration was 6.7 μM. The GalT was employed at a concentration of 4.5 mM. MnCl$_2$ at 5 mM, NaCl at 150 mM, and Tris buffer at 25 mM (pH 7.2). The UDP-sugar concentration tested was 0.3, 0.6, 1.2 and 1.8 mM. UDP-sugar at 0.6 mM was used for future reactions. The molecular ratio was calculated using the formula above. The results are shown in FIG. 11B.

Example 7

The optimised concentration of the payload (fluorophore-DIBO) concentration on the azide-alkyne cycloaddition reaction. The modified antibody (comprising the reactive sugar GalNAz) was employed at a concentration of 10.1 μM. MnCl$_2$ at 5 mM, NaCl at 150 mM, Tris buffer at 25 mM (pH7.2). The payload was tested using 4, 6, 8 or 10 equivalents. The molecular ratio was calculated as shown above. The results are shown in FIG. 12.

The invention claimed is:

1. A method of making an antibody conjugate, said method comprising the steps of:
   a) expressing an antibody from a CHO glycosylation mutant cell line encoding said antibody, wherein said CHO cell line is mutated such that N-glycans on antibodies produced by the cell have a terminal sugar which is N-acetyl glucosamine;
   b) reacting said N-acetylglucosamine with a reactive sugar in the presence of a GalT enzyme catalyst, to add said reactive sugar residue to the glycan, wherein the reactive sugar comprises a chemical functional group selected from a ketone, an aldehyde, an alkynyl, and an azide; and
   c) conjugating a payload to said ketone, aldehyde, alkynyl, or azide in the reactive sugar residue.

2. The method of claim 1, wherein the payload is selected from the group consisting of a toxin, a drug molecule, a polymer, an antibody, and an antigen-binding fragment of an antibody.

3. The method of claim 2, wherein the payload is a drug molecule.

4. The method of claim 2, wherein the payload is a toxin.

5. The method of claim 2, wherein the payload is a polymer.

6. The method of claim 1, wherein Click Chemistry is employed to conjugate the payload to the ketone, aldehyde, alkynyl, or azide functional group in the reactive sugar.

7. The method of claim 6, wherein the Click Chemistry is copper free chemistry.

8. The method of claim 3, wherein the drug molecule is a maytansinoid.

9. The method of claim 8, wherein the maytansinoid is selected from the group consisting of N 2'-deacetyl-N 2'(3-mercapto-1-oxopropyl)-maytansine (DM1), N 2'-deacetyl-N2'-(4-mercapto-1-oxopentyl)-maytansine (DM3), and N 2'-deacetyl-N 2'(4-methyl-4-mercapto-1-oxopentyl)-maytansine (DM4).

10. The method of claim 5, wherein the polymer is a natural polymer.

11. The method of claim 10, wherein the natural polymer is starch or albumin.

12. The method of claim 5, wherein the polymer is a synthetic polymer.

13. The method of claim 12, wherein the synthetic polymer is PEG.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Tyr Asn Ser Thr Tyr Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5
```